(12) United States Patent
Sari-Sarraf et al.

(10) Patent No.: US 7,601,978 B2
(45) Date of Patent: Oct. 13, 2009

(54) FABRIC WRINKLE EVALUATION

(76) Inventors: Hamed Sari-Sarraf, 2623 21$^{st}$ St., Lubbock, TX (US) 79410; Eric Hequet, 6607 Bangor Ave., Lubbock, TX (US) 79424; Christopher N. Turner, 5713 2nd Place Dr., Lubbock, TX (US) 79416; Aijun Zhu, 55 Fruit St., Bartlett Hall 505R, Boston, MA (US) 02114

( * ) Notice: Subject to any disclaimer, the term of this patent is extended or adjusted under 35 U.S.C. 154(b) by 576 days.

(21) Appl. No.: 10/411,359

(22) Filed: Apr. 11, 2003

(65) Prior Publication Data

US 2004/0245485 A1 Dec. 9, 2004

Related U.S. Application Data

(60) Provisional application No. 60/371,414, filed on Apr. 11, 2002.

(51) Int. Cl.
*G01L 5/04* (2006.01)

(52) U.S. Cl. .............. 250/559.08; 250/559.06; 250/559.07; 250/559.38; 250/559.39; 250/559.41; 356/238.1; 356/238.2; 356/238.3

(58) Field of Classification Search .......................... 250/559.06–559.08, 559.13, 559.38–559.41; 356/238.1–238.3; 382/111

See application file for complete search history.

(56) References Cited

U.S. PATENT DOCUMENTS

| | | | | |
|---|---|---|---|---|
| 4,160,913 A | * | 7/1979 | Brenholdt | 250/559.49 |
| 5,455,870 A | * | 10/1995 | Sepai et al. | 382/147 |
| 5,778,724 A | * | 7/1998 | Clapp et al. | 73/159 |
| 5,812,269 A | * | 9/1998 | Svetkoff et al. | 356/602 |
| 6,236,429 B1 | * | 5/2001 | Ho | 348/88 |
| 6,369,896 B1 | * | 4/2002 | Castello et al. | 356/430 |
| 6,563,130 B2 | * | 5/2003 | Dworkowski et al. | 250/559.33 |
| 6,603,103 B1 | * | 8/2003 | Ulrich et al. | 250/205 |
| 6,842,532 B2 | * | 1/2005 | Hu et al. | 382/111 |
| 2002/0054293 A1 | * | 5/2002 | Pang et al. | 356/430 |

FOREIGN PATENT DOCUMENTS

WO WO 0150835 A1 * 7/2001

OTHER PUBLICATIONS

Besma R. Abidi et al., Facet Model and Mathematical Morphology for Surface Characterization, Part of the SPIE Conference on Intelligent Robots and Computer Vision XVIII: Algorithms, Techniques, and Active Vision, SPIE vol. 3837, pp. 334-344.*

(Continued)

*Primary Examiner*—Georgia Y Epps
*Assistant Examiner*—Tony Ko
(74) *Attorney, Agent, or Firm*—Sonnenschein Nath & Rosenthal LLP

(57) ABSTRACT

Fabric wrinkles are automatically evaluated using a reliable, accurate, affordable, and efficient system. Two algorithms are used, the facet model algorithm and the plane-cutting algorithm, to extract features for evaluating wrinkles in fabrics. These algorithms eliminate the need for independent evaluation of a fabric specimen by a technician.

20 Claims, 20 Drawing Sheets

OTHER PUBLICATIONS

Tae Jin Kang, et al., "A New Objective Method of Measuring Fabric Wrinkles Using a 3-D Projecting Grid Technique," *Textile Res. J.*, 69(4), 261-268, 1999.

Tae Jin Kang, et al., "New Objective Evaluation of Fabric Smoothness Appearance," *Textile Res. J.*, 71(5), 446-453, 2001.

Xu, B. and D.F. Cuminato, "Evaluation of Fabric Smoothness Appearance Using a Laser Profilometer," *Textile Res. J.*, 68(12), 900-906, 1998.

* cited by examiner (a) No.1

(b) No. 2

(c) No. 3

(d) No. 3.5

(e) No. 4

(f) No. 5

FABRIC WRINKLE EVALUATION

CROSS-REFERENCE TO RELATED APPLICATIONS

This application claims the benefit, under 35 U.S.C. 119 (e), of U.S. Provisional Application No. 60/371,414 filed Apr. 11, 2002, the contents of which are incorporated herein by reference.

BACKGROUND OF THE INVENTION

1. Field of the Invention

The present invention relates to a method for determining the smoothness of fabric using image scanning.

2. Description of Related Art

In judging the aesthetic appeal of both apparel and household textiles, important concerns of consumers and researchers are focused on fabric wrinkle recovery and the wrinkle appearance after home laundering. Finding quantitative methods for evaluating wrinkling degrees of fabrics is one of the most important issues to researchers working in the field of fabric appearance retention and also to technicians assessing fabric characteristics. In the textile industry, currently there are two methods often used to grade wrinkles of a fabric. They are referred to as two AATCC Test Methods (TM): TM 124 and TM 128, each of which has one set of standard replicas used for comparison.

AATCC TM 128 is designed to rank the wrinkle degrees of textile fabrics after some wrinkles are induced. A test fabric specimen is wrinkled under a standard atmospheric condition in a standard wrinkling device. The device takes a predetermined load for a prescribed period of time to induce the fabric wrinkles. This specimen is then reconditioned and its appearance of wrinkles is evaluated. In this test method there are 5 standard replicas of different wrinkle degrees used for comparison.

For the standard test method of AATCC TM 124, standard procedures to rate wrinkles are specified. Under a standard lighting condition, three trained observers independently rate the wrinkling degree of a fabric specimen. They compare the appearance of the specimen with the smoothness of the appearances of six three-dimensional replicas. Each of the six replicas is made up of white plastic, representing a certain degree of wrinkling. This method is relatively simple and easy to perform. However, with the involvement of three trained technicians, it is very subjective in ranking wrinkling degrees of fabrics. Because of the subjectivity of the rating, one may question the credibility of the rating results: Are these wrinkle grades reliable? Are these grades repeatable or are these grades accurate? Actually one fabric might be ranked to belong to three different wrinkle levels by three observers, although these observers have been professionally trained to rank fabric wrinkles. In other words, grading results are usually biased by human perception. Sometimes it might be due to the subjective nature of human beings. Sometimes it might be due to the different regions attracting the attention of the three technician observers. Sometimes it might be due to the tilting angle when the fabric is held by observers during the rating processes.

Besides the questions on its reliability and accuracy, AATCC TM 124 is also expensive to execute. First, it needs at least three trained technicians. Second, this rating method should be performed in a standard lighting environment, which requires special rooms. Third, the standard replicas are expensive. In addition, a new set of replicas should be ordered and replaced every three years, because the combination of color aging and soiling from frequent usage may render the replicas unusable.

Therefore, it is desirable to develop a reliable, accurate, efficient and relatively economical system for automatically evaluating fabric wrinkles.

With the booming computer industry, image-processing techniques have been developed for various applications as well as for the textile industry. Image analysis has shown its potential application in objective evaluation of fabric appearances. It was reported that image-processing techniques have been developed to analyze fiber shape, yarn irregularity, and carpet appearance. It is suggested that image analysis is a good substitute for human inspection in fabric quality evaluation. Image analysis methods are increasingly adopted to obtain appearance characteristics because they are more repetitive, more reliable and more accurate than manual procedures. About eight years ago, a laser scanning system was developed to measure surface roughness and grade the pilling of fabrics. Computer image analysis techniques were designed to perform pill grading by matching the images of pilled fabrics with the images of a set of standard photographs representing various pilling appearances.

As to the evaluation of fabric wrinkles, some researchers have made contributions to the study of this field. As early as 1969, attempts were made to define the basic components of a wrinkle. Several descriptors were suggested, some of which provided a fair description of wrinkling such as wrinkle density, profile and randomness.

In 1995, fabric wrinkling was rated with intensity surface rations and shade area ratios by observing gray level intensity differences. In their approach, an HP color scanner was used so that an identical situation, such as illumination conditions and backgrounds, could be easily maintained. However, intensity images generated in this manner are not reliable indications. The features extracted from these images for wrinkle evaluation are not adequate to classify different kinds of fabric wrinkling, especially when the fabrics contain patterns or different colors.

Also considered were wrinkle density, profile, one-dimensional power spectrum density, sharpness, overall appearance and fractal dimension as feature parameters of fabric wrinkles. They were also using intensity images captured by a Sony CCD camera when replicas were illuminated from two corners by two light sources in a dark room. Based on the investigation and results, wrinkle surface ratio and standard deviation were suggested as feature parameters of wrinkle grades and a fractal theory was used to assess fabric wrinkles.

Using intensity images of the six standard replicas, the topographic labeling of the replicas using the facet model was analyzed. The surfaces of intensity gray level values were categorized into 11 labels. The percentages of the areas greater than and equal to 6, i.e., slopes, ridges, peaks, ravines, pits and saddles, were extracted as a feature to classify wrinkles on the replicas. Some interesting results were obtained concerning the relationship between grade numbers and the area percentages.

As mentioned above, all research on wrinkles was based on intensity images. Those techniques and algorithms suggested by researchers do not work properly to grade the wrinkling degrees of fabrics when fabrics have colored patterns.

Therefore, it is desirable to develop a new system that can objectively and accurately measure the smoothness of fabric appearances regardless of fabric patterns and colors. With laser-line projectors as light sources, such evaluation systems and algorithms have been developed with the help of image analysis. A laser-line triangulation method was used to measure the 3D surface of a wrinkled fabric with a 19-laser-line projector. A neural network was used to execute wrinkle classification with respect to the six standard replicas. Wrinkle parameters, such as arithmetic average roughness, root mean square roughness, 10-point height, and bearing-surface ratio, were fed into the neural network for training. In order to prevent or reduce the influence of wrinkle orientation, a rotating stage was required. In this system, some wrinkles of a fabric might be missed and some might be captured in a duplicated way. Recently, a stereovision algorithm was designed to evaluate fabric smoothness by fractal geometry. Because this method used two CCD cameras located at different angles together with two laser-line projectors over the detected objects, complicated calibrations are necessary to capture images of fabric wrinkles. Fractal dimension data were obtained as parameters of wrinkles, which fall between 2.015 and 2.035 for the 6 standard replicas.

BRIEF SUMMARY OF THE INVENTION

A new laser camera system has been set up to capture wrinkle images. Two new algorithms, the facet model and the plane-cutting, are designed to evaluate wrinkles without the influences of wrinkle orientation, colors or patterns of fabrics. In this laser camera system, a one-line laser projector is used. A camera is set up over a plane board, which is motorized to move back and forth. As a fabric or replica is placed on the board and moves along the direction controlled by the motor, the laser line scans the replica and the laser camera collects the information of laser intensity and wrinkle depths at the same time. The present invention focuses on the range image, which gets its name since its gray values are proportional to heights and depths of wrinkles. Based on the range image, the facet model is used. The topographic categories of the image are analyzed to rank wrinkles. Motivated by the facet model algorithm, the relatively simple plane-cutting algorithm is also developed.

The two algorithms of the present invention provide automatic evaluation of fabric wrinkles with objectivity and reliability. The results show that the two algorithms perform successfully to classify the 6 replicas, but for the fabric specimens, the wrinkle grades from both algorithms are not consistent with those assigned by technicians.

BRIEF DESCRIPTION OF THE DRAWINGS

The features and advantages of the present invention will become apparent from the following detailed description of a preferred embodiment, taken in conjunction with the accompanying drawings, in which.

DETAILED DESCRIPTION OF PREFERRED EMBODIMENTS

Figure 1:
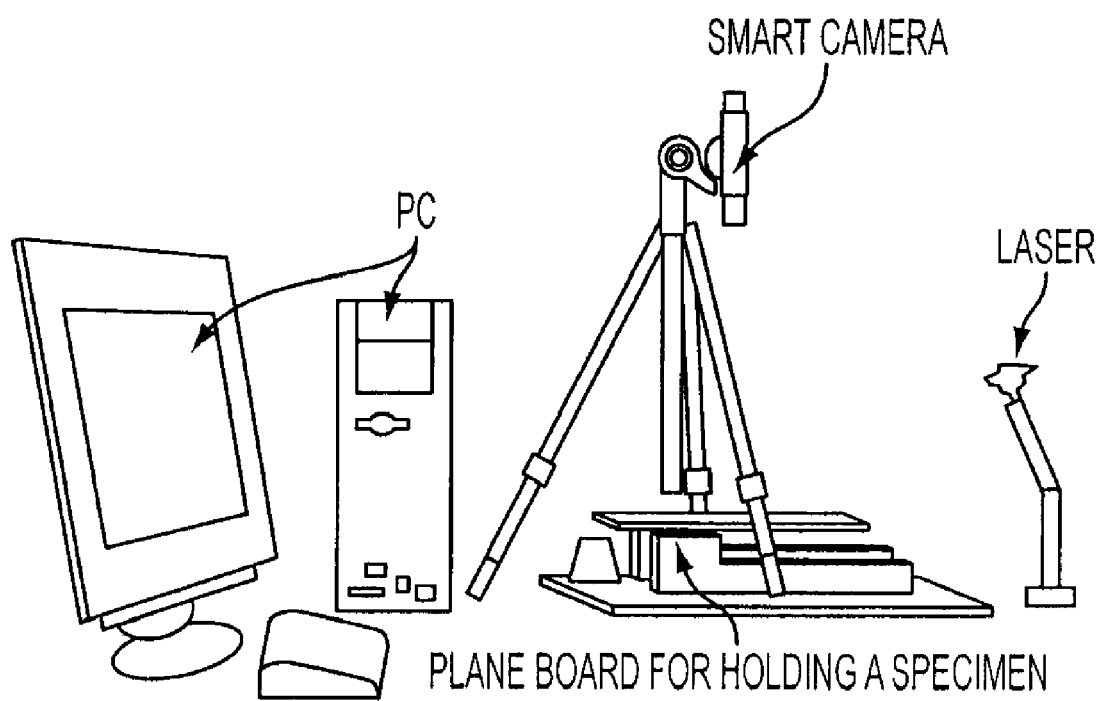
FIG. 1 shows a preferred embodiment of the laser camera system.

The laser camera system setup is mainly composed of a computer, a laser line projector, a moving plane board, and an IVP range camera with IVP smart vision sensor from Integrated Vision Products (IVP). A photo of the laser camera system is shown in FIG. 1.

The IVP range camera is equipped with a smart vision sensor, which is one of the internationally recognized products based on breakthrough technology created at IVP. The total integration of sensors, A/D converters and processors on one parallel-architecture chip allow image processing at an extremely high speed. More information may be referred to IVP. The power from the laser source is less than 5 microwatts and the wavelength of the laser is 600-700 nanometers. The focal point of the laser source can be adjusted and the laser line can be focused on a pre-determined target distance. The PC is installed with an IVP adapter board, and signals from the range camera can be collected by the PC.

Figure 2:
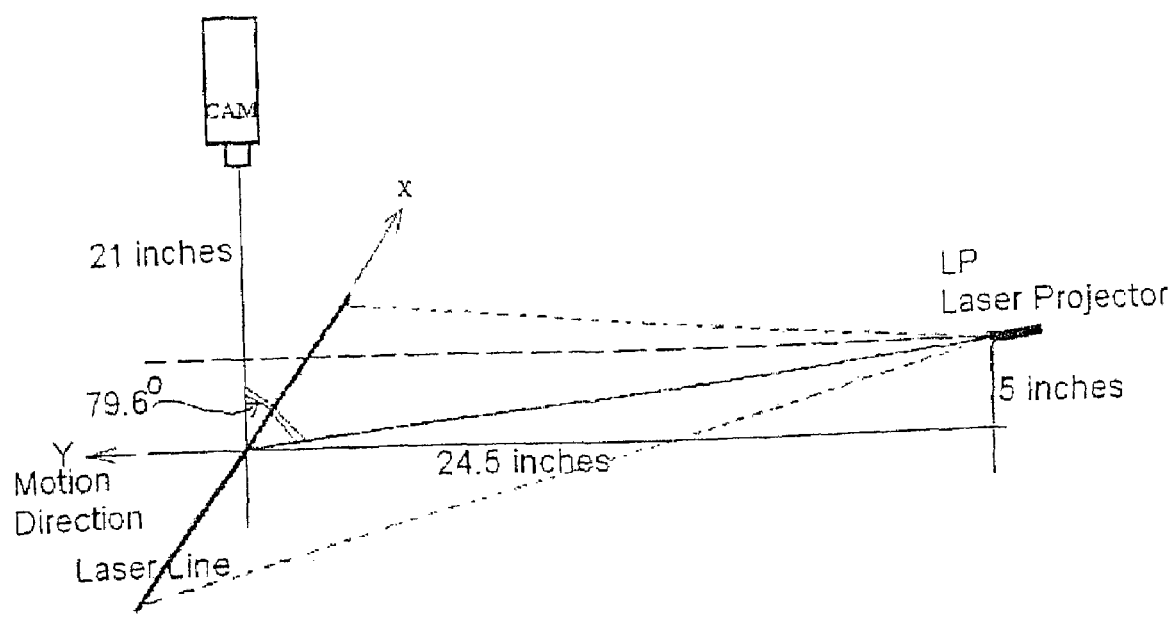
FIG. 2 shows a preferred embodiment of the laser camera system settings.

The schematic of the whole system is given in FIG. 2. The camera is set up directly over a horizontal plane board, which is used to hold fabrics or replicas. The distance between the camera and the plane board is 21 inches. The plane board is motorized to obtain motion along the Y direction, which is parallel to the optics plane of the entire system. The horizontal distance between the camera and the tilted laser projector is 24.5 inches. The laser projector is configured to transform a point laser beam into a line source and the projector is 5 inches higher than the moving board. The projection angle is about 79.6° between the laser line and the vertical direction. Keeping a large projection angle increases the height resolution of detected wrinkles. However, if this angle is set close to 90°, an occlusion problem occurs. This will become clearer after we check the triangulation of the settings referred to as sheet-of-light range imaging and how the IVP smart vision sensor works.

The range images are acquired using laser triangulation, which is a technique for measuring the range/depth of an object in the scene. This technique is based on the triangular relationships among the light source, camera and object. It is known under a variety of names such as sheet-of-light range imaging, laser profiling, and light-stripe ranging. In this work, we refer to it as sheet-of-light range imaging.

With the red laser as a dedicated source, the sheet-of-light range imaging is an active imaging technique. As a sheet (or stripe) of laser light is scanned over the object, one profile, or one row with 512 range pixels (the column pixel number M=512) is obtained. The range data and the relevant intensity points are marked. There are three ways to obtain a 512×512 range image: by moving the whole laser system apparatus over a static scene; by moving the scene; or by sweeping the sheet-of-light over a static 3D-scene with a mirror arrangement. In the presently preferred invention, the second approach is adopted: the plane board is motorized to carry a piece of replica or fabric. The scene is moved while the detecting sensor reads one profile every 2 ms (microsecond). All images used in this project are composed of 512 profiles, i.e., they are 512×512 range images.

Figure 3:
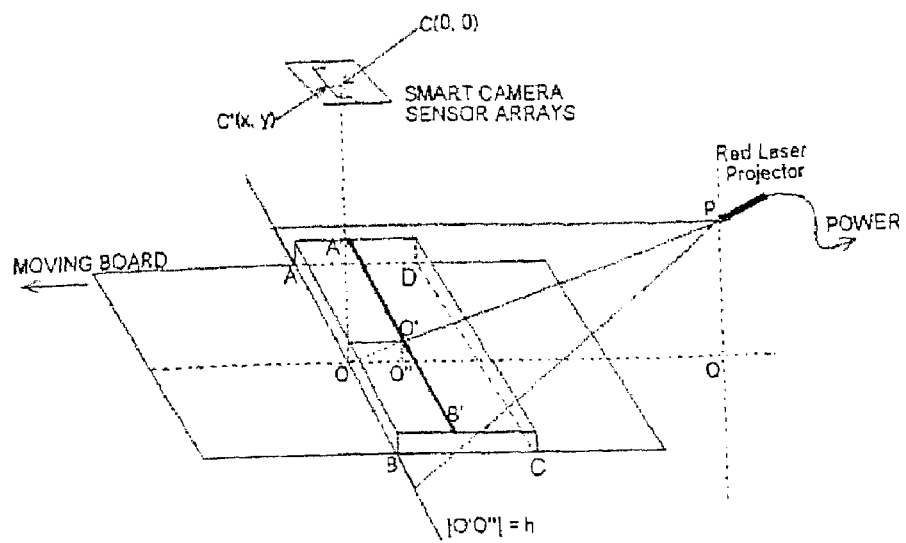
FIG. 3 shows the system geometry of triangulation: sheet-of-light range imaging.

The system geometry of triangulation is shown in FIG. 3. Before a lamina object ABCD of height h is laid on the moving board, the laser line is shining on the line AB. When the lamina is put on the board, the laser line is displaced to A'B' resulting from lamina blocking. The length of displacement OO" is the horizontal shift distance, which is proportional to the height h. OO" is calculated considering triangles of $\Delta OO'O''$ and $\Delta OPQ$:

$$OO''=O'O''(\tan \angle OO'O''), \quad \text{(Eq. 2.1b)}$$

$$OO''=h \cdot \tan \angle QPO. \quad \text{(Eq. 2.1b)}$$

The camera is aligned with the axis OC that is perpendicular to the moving board. Through the lens, the energy of laser reflection from the lamina triggers the sensor arrays of the smart camera shown in the top-center part of FIG. 3. The difference of sensor rows between C and C' is proportional to the displacement OO". The value of CC' is expressed as:

$$CC'=\alpha \cdot OO''=\alpha \cdot h \cdot \tan \angle QPO, \quad \text{(Eq. 2.2)}$$

where $\alpha$ is a coefficient related to the focal length of the lens, the distance between the camera and the object, and the camera magnification rate. Since these parameters are fixed, $\alpha$ is a constant. Therefore, if the heights of detected objects remain constant, the larger $\angle QPO$, the more sensor-rows the height displacement covers, and thus the larger the value of CC'. This means, as mentioned previously, that keeping a large projection angle $\angle QPO$ increases the resolution of wrinkle heights. To achieve infinite resolution, $\angle QPO$ has to be kept at 90°. However, infinite resolution is not practical because of the occlusion or blocking effect. Suppose there is another laminar object STUV (shown in FIG. 4) much higher than the object ABA'B', then the laser line is not able to reach the section of A'B'ST near to the lamina STUV. The section A'B'ST is hidden and blocked from the laser line. Experiments show that if $\angle QPO$ is kept around 80° the system works well to detect all levels of wrinkles of both the fabrics and the replicas.

Based on Eq. 2.2, the system maps height differences such as O'O" to displacement lengths such as CC' in the sensor array of the camera. Then the displacement lengths are normalized into a gray-level image (8-bit per pixel). This image is the range image.

Figure 5:
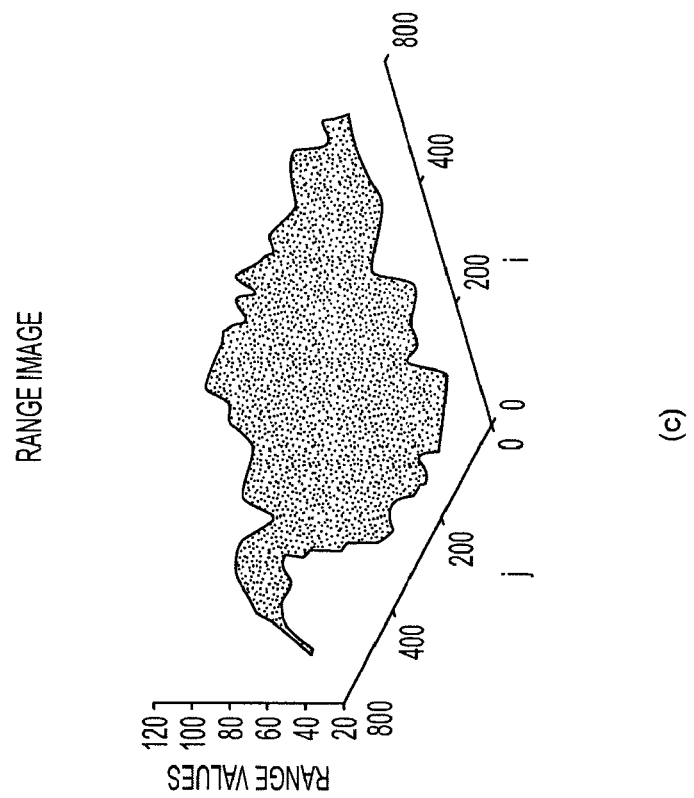
FIG. 5 shows an intensity image (a) and the ranges images 2D (b) and 3D (c)
Figure 5:
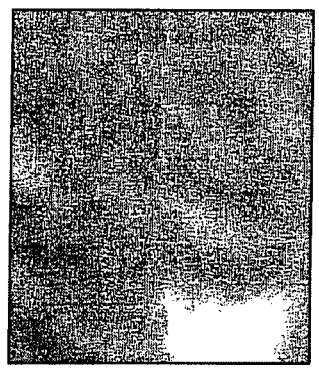
Figure 5:
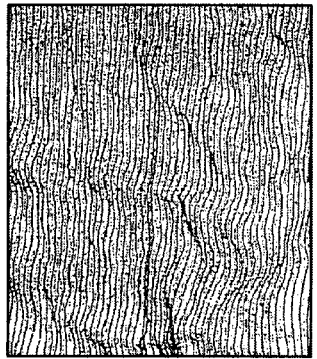

The smart camera system obtains intensity and range images at the same time with one scan. Only the range images will be used because of some patterns or different colors of fabrics. The intensity image, the range images in 2D and in 3D of one fabric sample are shown in FIG. 5 to explain why the intensity images are discarded.

Indeed the sample fabric has gray and yellow-green stripes. The gray stripes are wide and the yellow-green stripes are narrow. All stripes appear crooked due to the wrinkles in the fabric. Although the wrinkles on the sample are relatively small, it is obvious that the gray levels of the intensity image vary where there are wrinkles. However, if the intensity image is used to rate fabric wrinkling with methods such as the intensity surface ratio and shade area ratio, it is difficult to separate the wrinkles and the stripes unless some additional methods are applied to remove the stripes. In fact, there are many different and complicated color patterns in fabrics, and it is not practical to remove all the fabric patterns before ranking wrinkles.

Without the interference of stripes, the range image characterizes the wrinkle height well. Shown in FIG. 5(b) and (c), the range images change their gray levels with the occurrence of wrinkles. As explained above, the gray level of each pixel is proportional to the height of the corresponding wrinkle.

With the movement of the plane board, sheet-of-light range imaging covers a two-dimensional field of view on each fabric or replica. The size of the field of view is measured when the images of a square-scaled plane are captured. The size of the squares is 1×1 in².

Three points are marked in the intensity images: $P_1$ (365, 148), $P_2$ (370,346) and $P_3$ (175,338) so that the distances are $P_1P_2$=3 inches and $P_2P_3$=3 inches. Setting the resolutions X pixels/inch along the row direction, and Y pixels/inch along the column direction, the following equations are written:

$$\frac{(365-370)^2}{X^2} + \frac{(148-346)^2}{Y^2} = 3^2, \quad \text{(Eq. 2.3)}$$

$$\frac{(370-175)^2}{X^2} + \frac{(346-338)^2}{Y^2} = 3^2. \quad \text{(Eq. 2.4)}$$

The solutions of X and Y are 65.0531 and 66.0217 pixels/inch, respectively. For range images, the field of view is 7.8705×7.7550 in². The replica size is 12×13 inches and the size of the fabric specimens is 14×15 in². It is noted that the central parts of fabric specimens are the regions of interest, since we want to get rid of effects from hemmed fabric borders. The images captured by the laser camera system cover about 40% of the whole replica areas. Images of three parts of each replica are captured: the central (CTR), bottom-left (BL) and upper-right (UR) areas. Each part covers about 30% of the entire fabric area. Although a 7.8705×7.7550-in² area is small, it is large enough to include wrinkle information of each fabric and replica while preventing effects of hemmed fabric borders at the same time.

The wrinkle depths on each replica or fabric sample are represented by pixel values in the range images. The depth/range resolution is measured with the help of a 0.05-inch thick CD. The pixel values of the CD range image are 30 higher than those of the plane board. So the depth resolution can be obtained as:

$$\frac{0.05 inches}{30} \times 25400 \text{ }\mu m/inches = 42.3 \text{ }\mu m \qquad (Eq. 2.5)$$

which is adequate for the system to capture any levels of wrinkles except those creases less than 42 μm in depth on the No. 3 replica. Some creases shown in the intensity images are lost in the range images.

Observed from the images of the CD, there are limitations of the laser camera system: (1) the objects of interest cannot be transparent, (2) the detected objects cannot be completely reflective, and (3) it is desired that the discrepancy of depths all over the object should not be large enough to cause occlusion. especially for objects with big bumps. Fortunately, the replicas and fabrics are neither transparent nor completely reflective. With an appropriate projection angle of the laser line, any occlusion may be prevented even if there are bumps on the fabrics and replicas. A more detailed discussion regarding bumps will be covered in the next chapter.

Facet Model Algorithm

To extract a feature that describes wrinkle degrees from the range-images, the facet model algorithm is developed consisting of the following steps:

1. A range image is first processed by a notch filter.
2. Then it is passed through two low-pass filters with different window sizes, generating two blurred images.
3. A difference image is obtained by subtracting the two blurred images.
4. The facet model is used and the difference image is treated as a piecewise-continuous gray level surface around each pixel by applying bivariate-cubic polynomials to approximate this surface.
5. Topographic categories on the continuous surfaces are calculated.
6. The pixel areas of hillside slopes, ridges, peaks, ravines and pits are summed up as a feature to describe the degrees of wrinkles.

Figure 6:
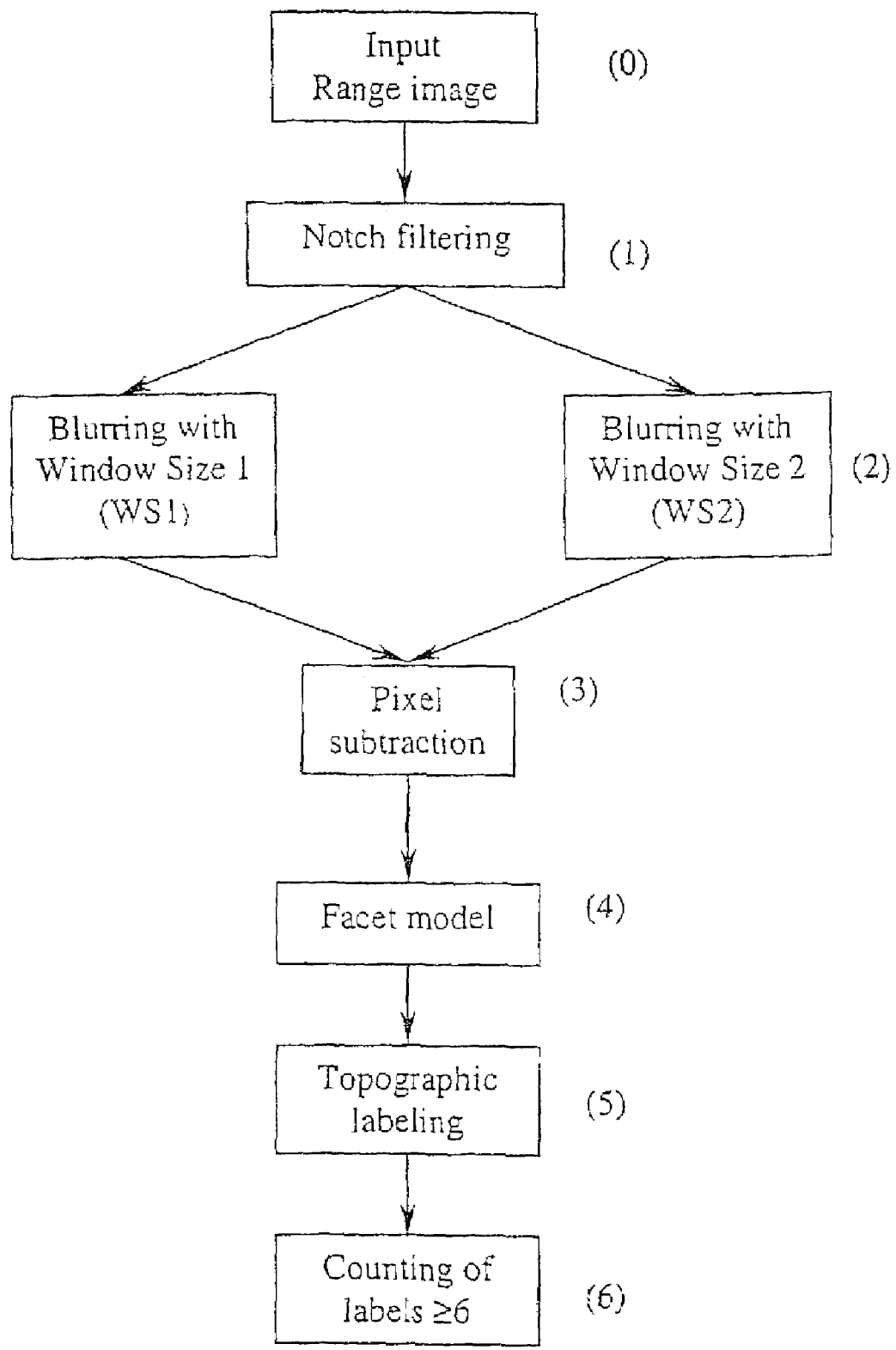
FIG. 6 is a flow chart of the facet model algorithm.

The facet model algorithm flow chart is shown in FIG. 6. The input image is the range image captured by the laser camera system. Below is a detailed description of the algorithm.

The laser camera system has such a high resolution of 42 μm that weaving patterns of fabrics show up in the range images. The weaving patterns are composed of tiny lines in the horizontal direction. For fabric samples with smooth surfaces labeled as No. 3.5, No. 4 or No. 5, their texture-weaving patterns may seriously affect topographic labeling operation. To solve this problem, preprocessing such as applying a notch filter to the range image is necessary.

Considered as an example to illustrate the notch filtering, this patterned fabric image is first processed by an FFT (Fast Fourier Transform) and its transformed image in the frequency domain is shown. The frequency components of the weaving patterns are marked. The notch filtering is performed in this frequency domain. The notch filter is defined by removing the components of the four 80×160.

This notch filter is used for filtering the frequency components of weaving patterns and at the same time this filtering operation retains the other frequency components as much as possible. In our experimental fabric specimens, all the weaving patterns are the vertical or horizontal lines therefore, their frequency components are located at the horizontal axes or the vertical axes in the Fourier spectra of the range images. This is the reason why this notch filter is chosen to remove the weaving patterns of fabrics.

This frequency filter is ideal because only the frequencies outside those rectangles pass without any attenuation while any of those frequencies inside those rectangles cannot pass. That means there is a sharp discontinuity that sets up a clear cutoff between passed and filtered frequencies. The ideal filter introduces ringing artifacts in the filtered image. However, no negative effects from ringing have been found in the following operations of the algorithm. If the ringing artifacts are unacceptable, other filters (such as a Butterworth low-pass filter and an exponential low-pass filter) can be used.

Finally an IFFT (Inverse Fast Fourier Transform) is applied to the low-frequency components. After the notch-filtering operation is performed, we obtain the filtered image free of weaving patterns. Besides, the filtered image has an additional advantage: The image is blurred, which is desirable in the following operations.

Thus, we achieve our goal and get a blurred image at the same time. However, the image is not smooth enough, further smoothing will be carried out in the next step.

After removing the interference from the weaving patterns, blurring with different window sizes and pixel subtraction are applied to further highlight the wrinkles and eliminate the interference from bumps. It is found that bumps of different sizes are often mixed with wrinkle heights/depths in the range images. Pixel subtraction is used to remove the bump effects. The No. 3 replica is now taken as an example to illustrate the steps: blurring and subtraction.

The 2D and 3D versions of the range images of the No. 3 replica are observed showing the that the range image of the replica has bumps, which are characterized as come large areas of different brightness. It is obvious that the bumps are mixed with the wrinkles of the No. 3 replica. The filtered image from the previous step is shown where the bumps still exist. To eliminate this kind of mixing between bumps and wrinkles, pixel subtraction is used to extract wrinkles only. During blurring, the boundaries are ignored without any negative effect.

Resulting images $A_{WS1}$ and $B_{WS2}$ from blurring with the window size 91 (WS1=91) and window size 5 (WS2=5), respectively, are produced. Generally, it is desired that WS1 be larger than WS2. The difference image after the pixel-by-pixel subtraction of the two blurred images ($B_{WS2}-A_{WS1}$) were produced. During the subtraction, the image $A_{WS1}$ is considered as a background with bumps, and this background is subtracted from the image $B_{WS2}$. The bump exists in the original image. In the difference image, it is obvious that the bumps are removed. It is noted that after the subtraction, the values of each pixel might be negative, zero or positive.

The resulting images from the notch filter in the previous step are always still noisy because of the appearance properties of the fabric specimens. The fabric specimens always have hairiness, more or less. So WS2 is chosen to be greater than or equal to 5 in order to obtain the desired smoothening effects.

Actually, the subtraction does affect the wrinkle properties. The image $A_{WS1}$ shown is considered as a background that contains more or less information about the wrinkles. This wrinkle information is lost after the operation of pixel subtraction. The extent of this effect depends on WS1, WS2 together with the sizes and widths of the wrinkles. Here WS1 is chosen as large as 91 to decrease this extent from subtraction.

The facet model is a powerful tool to estimate a smooth surface of the neighborhood around a certain pixel. It has been used for the detection of edges, corners, curves and ridges, and surface topography analysis.

The commonly used forms for the facet model include: piecewise constant (flat facet model), piecewise linear (sloped facet model), piecewise quadratic and piecewise cubic. In the flat model, each ideal region in the image is constant in gray level. In the sloped model, each ideal region has a gray level surface that is a sloped plane. Similarly, in the quadratic and cubic models, regions have gray level surfaces that are bivariate quadratic and cubic surfaces, respectively. The facet model used in this project is the piecewise cubic.

Figure 7:
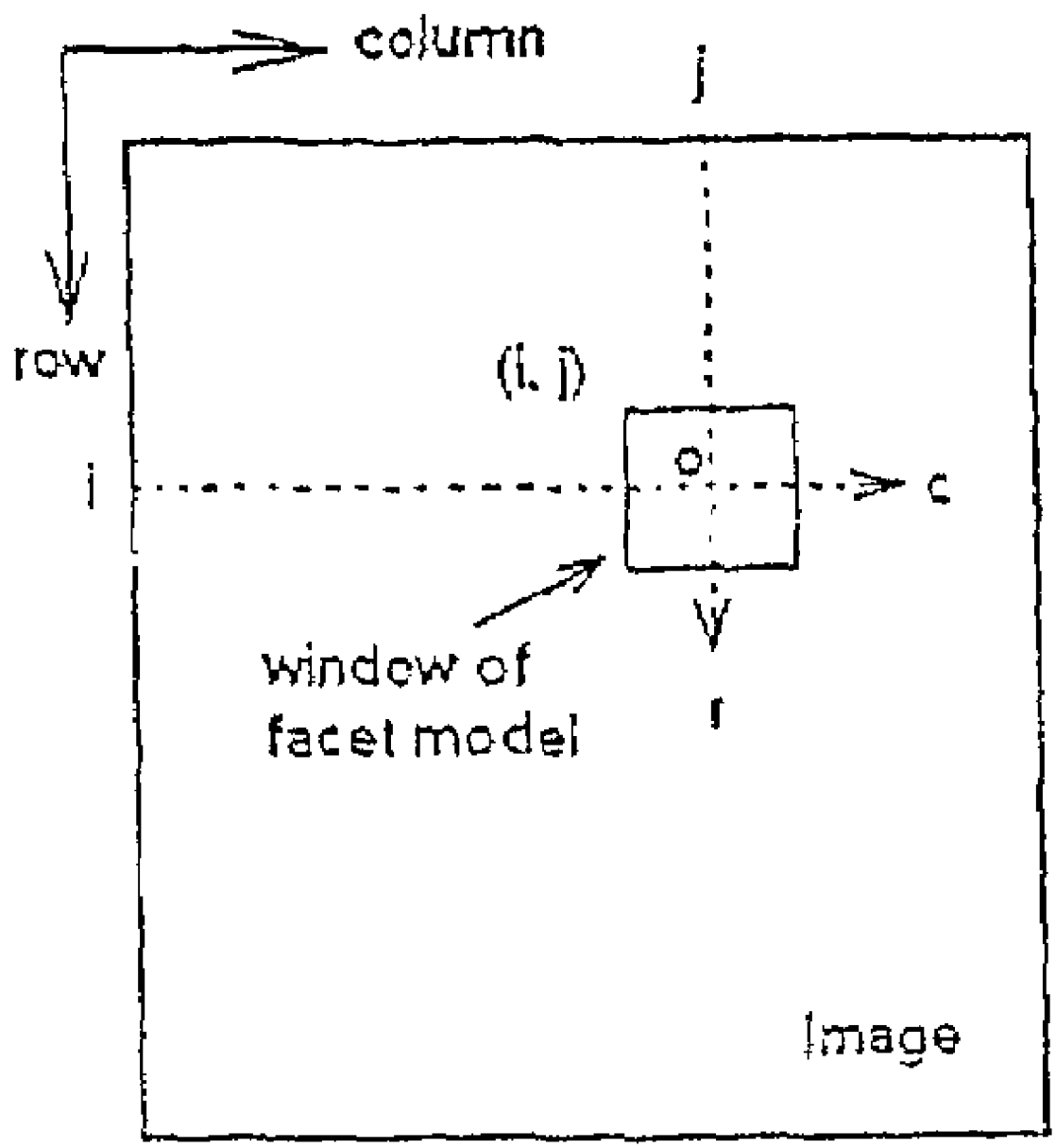
FIG. 7 shows the relationship between image pixel (i,j) and facet model coordinates (r,c)
Figure 8:
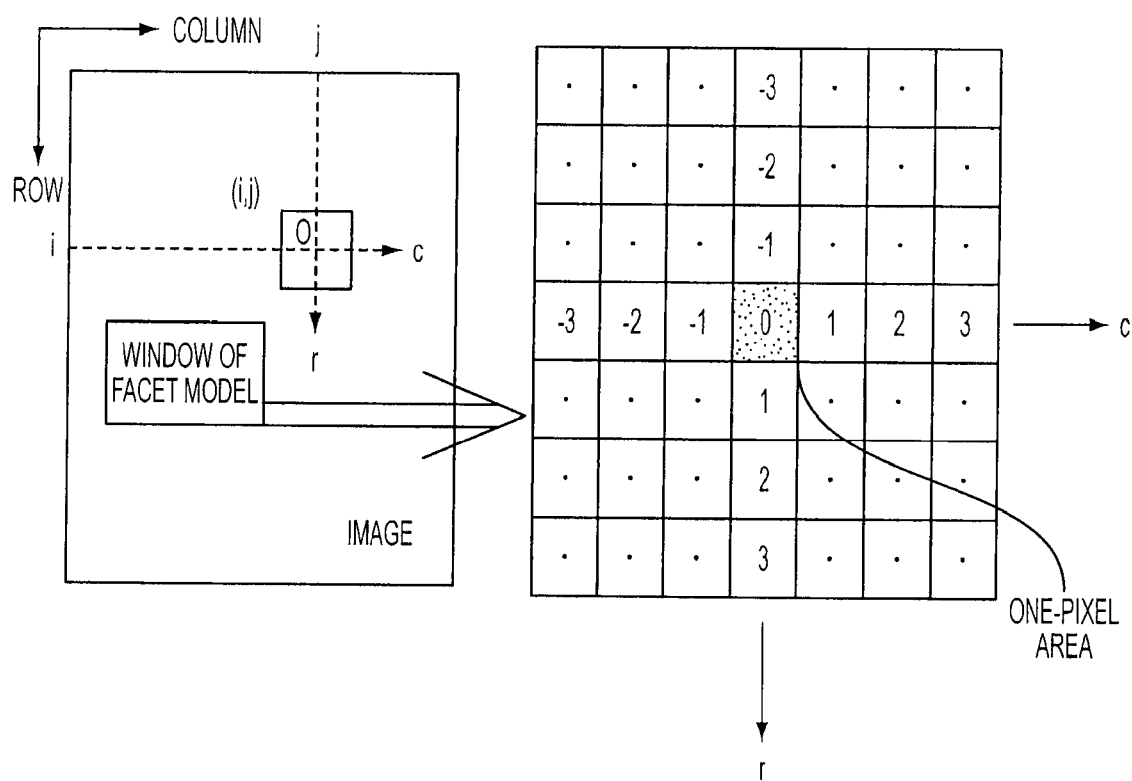
FIG. 8 illustrates the facet model window (7×7)

Two coordinates are defined in the facet model. One is the image coordinate and (i,j) represents the pixel of row i and column j. The other is the coordinate of the facet model window ($\Psi$) and (r,c) represents the point of row r and column c. A pixel (i,j) in an image is set as the origin (0,0) in the coordinate of $\Psi$. Here i and j are only integers, and r and c can be any real data. The relationship between the image pixel (i,j) and the point (r,c) of the facet model window is shown in FIG. 7, For example, FIG. 8 shows a window of 7×7 in the coordinate (r,c). Here it is assumed that the points (r,c) when r and c are integers, such as (0,0), (1,0), (−1,0), (0,1) and so on, are located at the center of each pixel in the image. That will bring in one problem for the application of topographic labeling, which will be discussed in the implementation of topographic labeling later.

The estimation function f for the facet model takes the bivariate cubic form, $$f(r,c)=k_1+k_3r+k_2c+k_4r^2+k_5rc+k_6c^2+k_7r^3+k_8r^2c+k_9rc^2+k_{10}c^3, \quad \text{(Eq. 3.1)}$$

to fit a neighborhood area of the pixel (i,j). This neighborhood is always defined as a square window of a certain size (ws× ws) and centered at the pixel (i,j), which is the origin (r,c)= (0,0).

The set $\{k_1,k_2,k_3, \ldots, k_{10}\}$ used in Eq. 3.1 is a group of coefficients that are different for each pixel of the entire image. Such functions of Eq. 3.1 are easily represented as linear combinations of the polynomials in any polynomial basis set. The easiest set is a polynomial basis set permitting the independent estimation of each coefficient. Such a basis set is the set of discrete orthogonal polynomials. That is, the basis set holds polynomials that are mutually orthogonal and such a basis set is mutually orthogonal.

According to the Gram-Schmidt Orthogonalization Procedure, there is an inductive technique to generate a mutually orthogonal set from any linearly independent set. The term of "linear independence" is defined as follows:

In a vector space S, if the elements of $\{x_1, x_2, \ldots, x_n\}$ belong to the vector space S, then a combination $x=l_1x_1+l_2x_2+\ldots+l_nx_n$ is also in the vector space S. The combination x is said to be a linear combination of $x_1, x_2, \ldots, x_n$. When $l_1x_1+l_2x_2+\ldots+l_nx_n=0$, if the only linear combination of $x_1, x_2, \ldots, x_n$ has all $l_j$ equal to zero, the set $\{x_1, x_2, \ldots, x_n\}$ is said to be linearly independent.

Here in our problem, $$\{x_1,x_2, x_3, \ldots x_{10}\}=\{1, r, c, r^2, rc, c^2, r^3, r^2c, rc^2, c^3\} \quad \text{(Eq. 3.2)}$$

is a set of functions that are linearly independent. Suppose a mutually orthogonal set is generated by the inductive technique:

$$\{P_1, P_2, P_3, \ldots, P_{10}\} \quad \text{(Eq. 3.3)}$$

After setting $P_1=x_1$, the set elements $P_i (i=2,3 \ldots ,10)$ are obtained from the following inductive equation:

$$p_n = x_n - \sum_{j=1}^{n-1} \frac{<x_n, P_j> P_j}{<P_j, P_j>}, n = 2, 3, 4 \ldots , 10, \quad \text{(Eq. 3.4)}$$

where <,> means the inner product or dot product. It is noted that the region of the inner product covers the whole region ($\Psi$) of each facet model window. Therefore each set of such discrete orthogonal polynomials is definitely dependent on the facet model window size. For example, if the window size is chosen as 5 (ws=5), the basis set of orthogonal polynomials is calculated as follows $$\text{(Eq. 35)}$$

| $P_1(r, c) = 1$ | $P_2(r, c) = r$ | $P_3(r, c) = c$ |
| $P_4(r, c) = r^2 - 2$ | $P_5(r, c) = rc$ | $P_6(r, c) = c^2 - 2$ |
| $P_7(r, c) = r^3 - 3.4r$ | $P_8(r, c) = r^2c - 2c$ | $P_9(r, c) = rc^2 - 2r$ |
| $P_{10}(r, c) = c^3 - 3.4c$ | | |

If the window size is set as 11 (ws=11), the basis set of orthogonal polynomials is different from that of ws=5:

$$\text{(Eq. 3.6)}$$

| $P_1(r, c) = 1$ | $P_2(r, c) = r$ | $P_3(r, c) = c$ |
| $P_4(r, c) = r^2 - 10$ | $P_5(r, c) = rc$ | $P_6(r, c) = c^2 - 10$ |
| $P_7(r, c) = r^3 - 17.8r$ | $P_8(r, c) = r^2c - 10c$ | $P_9(r, c) = rc^2 - 10r$ |
| $P_{10}(r, c) = c^3 - 17.8c$ | | |

Thus, a mutually orthogonal set obtained is used to calculate the coefficients of Eq. 3.1. If exact fitting occurs, Eq. 3.1 is rewritten as:

$$f(r, c) = d(r, c) = \sum_{n=1}^{N=10} a_n P_n(r, c). \quad \text{(Eq. 3.7)}$$

Note d(r,c) is the neighborhood gray-level data over the whole window $\Psi$ around a pixel (i, j). Here $a_n$'s are a group of new coefficients that are functions of $k_n$'s, i.e., $$a_n=a_n(k_1, k_2, k_3, \ldots, k_{10}), n=1, 2, \ldots 10. \quad \text{(Eq. 3.8)}$$

In other words, $k_n$'s can be obtained after the coefficients of $a_n$'s are calculated, i.e., $$k_n=k_n(a_1, a_2, a_3, \ldots, a_{10}), n=1, 2, \ldots 10. \quad \text{(Eq. 3.9)}$$

Note that both $k_n$'s and $a_n$'s are constants for each pixel (i,j). It means that calculating the coefficients of $k_n$ is equivalent to calculating these coefficients of $a_n$. $a_n$'s are obtained with the equal-weighted least-squared fitting method. Let (r, c)$\in \Psi$, the approximate fitting problem is to determine coefficients $a_n$ (n=1, 2, . . . 10) such that $$e^2 = \sum_{(r,r)\in\Psi} \left[ d(r, c) - \sum_{n=1}^{10} a_n P_n(r, c) \right]^2 \quad \text{(Eq. 3.10)}$$

is minimized (e is the error between the fitting value and the gray-level data). The result is $$a_m = \frac{\sum_{(r,r)\in\Psi} P_m(r,c)d(r,c)}{\sum_{(r,r)\in\Psi} P_m^2(r,c)}, m = 1, 2, \ldots, 10 \quad \text{(Eq. 3.11)}$$

Actually the convenience of using an orthogonal basis set appears during the procedure of solving for $a_m$ since the values of $$\sum_{(r,c)\in\Psi} P_m(r,c) \sum_{(r,c)\in\Psi} P_{m'}(r,c),$$

(m=1,, 2, ..., 10) and m'=1, 2, ..., 10) are zero if m≠m'.

Eq. 3.11 is interesting because it means that each fitting coefficient $a_m$ can be computed as a linear combination of the gray level data of d(r,c). For each pixel over the related window $\Psi$, the gray level value d(r,c) is multiplied by the weight $$\frac{P_m(r,c)}{\sum_{(r,r)\in\Psi} P_m^2(r,c)}, \quad \text{(Eq. 3.12)}$$

which is just an appropriate normalization of an evaluation of the polynomial $P_m$ at the index (r,c). According to Eqs. 3.11 and 3.12, there are some filters that are used to calculate these coefficients of $a_n$ around each pixel in the image. For example, using Eq. 3.5, the weights of Eq. 3.12 for the 5×5 neighborhood are shown in Table 1.

These kinds of weights are called the kernels of the facet model.

| $k_7 = a_7$ | $k_8 = a_8$ | $k_9 = a_9$ |
| $k_{10} = a_{10}$ | | |

For each pixel of an image, there is a group of coefficients of $k_n$'s for the facet model. Therefore if an image has M×N pixels, then there are M×N groups of coefficients of $k_n$'s. In other words, all $k_n$'s are functions of (i,j): $k_n = k_n(i,j)$, n=1, 2, ..., 10. It is noted that the facet model window may overlap outside the boundaries of the image. No consideration is granted to these boundary pixels. As mentioned before, the boundary pixels are ignored without any negative effect.

Once the fitting coefficients have been calculated, the estimated polynomials for all pixels of the image are given by Eq. 3.1. It should be noted that there is a kind of approximation in calculating these coefficients. The function of Eq. 3.1 is considered as a combination of discrete polynomials around the region $\Psi$ while calculating these coefficients. After this, the function of Eq. 3.1 is considered as being continuous around the region $\Psi$. This continuous function always permits us to obtain the first and second directional derivatives at any point. Then it is possible to process topographic labeling.

The derivatives of 2D functions are directional. For the function in Eq. 3.1, the directional derivative in the direction $\alpha$ is defined as $$f'_\alpha(r,c) = \lim_{h\to 0} \frac{f(r+h\sin\alpha, c+h\cos\alpha) - f(r,c)}{h}. \quad \text{(Eq. 3.14)}$$

The direction $\alpha$ is the clockwise angle starting from the column axis. Directly from the above definition,

TABLE 1

$1/25 \ a_1 \ 1$:
| 1 | 1 | 1 | 1 | 1 |
| 1 | 1 | 1 | 1 | 1 |
| 1 | 1 | 1 | 1 | 1 |
| 1 | 1 | 1 | 1 | 1 |
| 1 | 1 | 1 | 1 | 1 |

$1/50 \ a_2 \ r$:
| -2 | -2 | -2 | -2 | -2 |
| -1 | -1 | -1 | -1 | -1 |
| 0 | 0 | 0 | 0 | 0 |
| 1 | 1 | 1 | 1 | 1 |
| 2 | 2 | 2 | 2 | 2 |

$1/50 \ a_3 \ c$:
| -2 | -1 | 0 | 1 | 1 |
| -2 | -1 | 0 | 1 | 1 |
| -2 | -1 | 0 | 1 | 1 |
| -2 | -1 | 0 | 1 | 1 |
| -2 | -1 | 0 | 1 | 1 |

$1/70 \ a_4 \ (r^2-2)$:
| 2 | 2 | 2 | 2 | 2 |
| -1 | -1 | -1 | -1 | -1 |
| -2 | -2 | -2 | -2 | -2 |
| -1 | -1 | -1 | -1 | -1 |
| 2 | 2 | 2 | 2 | 2 |

$1/100 \ a_5 \ rc$:
| 4 | 2 | 0 | -2 | -4 |
| 2 | 1 | 0 | -1 | -2 |
| 0 | 0 | 0 | 0 | 0 |
| -2 | -1 | 0 | 1 | 2 |
| -4 | -2 | 0 | 2 | 4 |

$1/70 \ a_6 \ (c^2-2)$:
| 2 | -1 | -2 | -1 | 2 |
| 2 | -1 | -2 | -1 | 2 |
| 2 | -1 | -2 | -1 | 2 |
| 2 | -1 | -2 | -1 | 2 |
| 2 | -1 | -2 | -1 | 2 |

$1/50 \ a_7 \ (r^3-3.4r)$:
| -1 | -1 | -1 | -1 | -1 |
| 2 | 2 | 2 | 2 | 2 |
| 0 | 0 | 0 | 0 | 0 |
| -2 | -2 | -2 | -2 | -2 |
| 1 | 1 | 1 | 1 | 1 |

$1/140 \ a_8 \ (r^2c-2c)$:
| -4 | -2 | 0 | 2 | 4 |
| 2 | 1 | 0 | -1 | -2 |
| 4 | 2 | 0 | -2 | -4 |
| 2 | 1 | 0 | -1 | -2 |
| -4 | -2 | 0 | 2 | 4 |

$1/140 \ a_9 \ (rc^2-2r)$:
| -4 | 2 | 4 | 2 | -4 |
| -2 | 1 | 2 | 1 | -2 |
| 0 | 0 | 0 | 0 | 0 |
| 2 | -1 | -2 | -1 | 2 |
| 4 | -2 | -4 | -2 | 4 |

$1/50 \ a_{10} \ (c^3-3.4c)$:
| -1 | 2 | 0 | -2 | 1 |
| -1 | 2 | 0 | -2 | 1 |
| -1 | 2 | 0 | -2 | 1 |
| -1 | 2 | 0 | -2 | 1 |
| -1 | 2 | 0 | -2 | 1 |

After obtaining the coefficients ($a_1, a_2, a_3, \ldots, a_{10}$), it is easy to get the coefficients ($k_1, k_2, k_3, \ldots, k_{10}$). That is, for the 5×5 facet model the coefficients $k_n$'s are as follows:

$$k_1 = a_1 - 2\cdot(a_4 + a_6) \quad k_2 = a_2 - 3.4a_7 - 2a_9 \quad k_3 = a_3 - 2a_3 - 3.4a_{10}$$
$$k_4 = a_4 \quad k_5 = a_5 \quad k_6 = a_6 \quad \text{(Eq. 3.13)}$$

$$f'_\alpha(r,c) = \frac{\partial f(r,c)}{\partial r}\sin\alpha + \frac{\partial f(r,c)}{\partial c}\cos\alpha. \quad \text{(Eq. 3.15)}$$

The second derivative in the direction $\alpha$ at the point (r,c) is $$f''_\alpha(r, c) = \quad \text{(Eq. 3.16)}$$

$$\frac{\partial^2 f(r,c)}{\partial r^2}\sin^2\alpha + \frac{\partial^2 f(r,c)}{\partial r\partial c}\sin\alpha\cos\alpha + \frac{\partial^2 f(r,c)}{\partial c^2}\cos^2\alpha.$$

The gradient of the function at (r,c) is a vector whose magnitude is given by $$\sqrt{\left(\frac{\partial f}{\partial r}\right)^2 + \left(\frac{\partial f}{\partial c}\right)^2}. \quad \text{(Eq. 3.17)}$$

This magnitude is the maximum rate of change of the function at the point (r,c) with its angle, $$\beta = \tan^{-1}\left(\frac{\partial f/\partial r}{\partial f/\partial c}\right). \quad \text{(Eq. 3.18)}$$

Along the direction of β, the function has the greatest change rate.

The following notation is used to describe the mathematical properties of the topographic categories for continuous smooth surfaces expressed by f (r,c)
∇f The gradient vector of the function f (r,c)
‖∇f‖ The gradient magnitude
$\overline{\omega}_{(1)}$ The unit vector in the direction where the second directional derivative has the greatest magnitude
$\overline{\omega}_{(2)}$ The unit vector that is orthogonal to $\overline{\omega}_{(1)}$
$\lambda_1$ The second directional derivative in the direction of $\overline{\omega}_{(1)}$
$\lambda_2$ The second directional derivative in the direction of $\overline{\omega}_{(2)}$
∇f·$\overline{\omega}_{(1)}$ The first directional derivative in the direction of $\overline{\omega}_{(1)}$
∇f·$\overline{\omega}_{(2)}$ The first directional derivative in the direction of $\overline{\omega}_{(2)}$
Without loss of generality, inequality $|\lambda_1|\geq|\lambda_2|$ is assumed.

The five partial derivatives encountered here, ∂f/∂r, ∂f/∂c, $\partial^2 f/\partial r^2$, $\partial^2 f/\partial r\partial c$, and $\partial f^2/\partial c^2$, have to be approximated in order to calculate the parameters listed above. The 2×2 Hessian matrix is introduced to calculate $\lambda_1, \lambda_2, \overline{\omega}_{(1)}$ and $\overline{\omega}_{(2)}$. The Hessian matrix is $$H = \begin{pmatrix} \partial^2 f/\partial r^2 & \partial^2 f/\partial r\partial c \\ \partial^2 f/\partial r\partial c & \partial^2 f/\partial c^2 \end{pmatrix}. \quad \text{(Eq. 3.19)}$$

The matrix satisfies the following equations:

$$H\overline{\omega}_{(1)}=\lambda_1\overline{\omega}_{(1)}, H\overline{\omega}_{(2)}=\lambda_1\overline{\omega}_{(2)}. \quad \text{(Eq. 3.20)}$$

That is, $\lambda_1, \lambda_2, \overline{\omega}_{(1)}$ and $\overline{\omega}_{(2)}$ can be obtained by calculating the eigenvalues and eigenvectors of the Hessian matrix.

Based on ‖∇f‖, $\lambda_1, \lambda_2$, ∇f·$\overline{\omega}_{(1)}$ and ∇f·$\overline{\omega}_{(2)}$, the mathematical criteria for topographic labeling are shown in Table 3.1. In the table '+', '0', and '−' represent that the values are positive, zero or negative, respectively. '*' means "DO NOT CARE", which means the relevant parameter might be set to be any value. It is noted that '0' here actually means "not significantly different from zero". The last column contains the label values ranging from 1 (flat) to 10 (pit) corresponding to topographic categories.

In fact, the classification criteria listed in Table 2 cannot be directly used because there is a problem when applying the classification in a one-pixel area. If the topographic classification is only applied to the point, the center of each pixel, then for example, a pixel having a peak near one of its corners might be misclassified as a concave hill rather than as a peak. On one hand, the topographic classification must be a sampling of the actual topographic surface classes. On the other hand, it is most likely that some categories like peak, pit, ridge, ravine and saddle might never occur precisely at a pixel's center. Not occurring precisely at a pixel's center, they might occur just around that one-pixel area. If these cases occur, the pixels should be classified as those categories rather than the classification labels of the pixels' center points.

TABLE 2

| ‖∇f‖ | $\lambda_1$ | $\lambda_2$ | ∇f·$\overline{\omega}_{(1)}$ | ∇f·$\overline{\omega}_{(2)}$ | Topographic Categories | Labels |
|---|---|---|---|---|---|---|
| 0 | − | − | 0 | 0 | Peak | 8 |
| 0 | − | 0 | 0 | 0 | Ridge | 7 |
| 0 | − | + | 0 | 0 | Saddle | 2 |
| 0 | 0 | 0 | 0 | 0 | Flat | 1 |
| 0 | + | − | 0 | 0 | Saddle | 2 |
| 0 | + | 0 | 0 | 0 | Ravine | 9 |
| 0 | + | + | 0 | 0 | Pit | 10 |
| + | − | − | ≠0 | ≠0 | Hillside (concave) | 4 |
| + | − | * | 0 | * | Ridge | 7 |
| + | * | − | * | 0 | Ridge | 7 |
| + | − | 0 | ≠0 | * | Hillside (concave) | 4 |
| + | − | + | ≠0 | ≠0 | Hillside (saddle) | 5 |
| + | 0 | 0 | * | * | Hillside (slope) | 6 |
| + | + | − | ≠0 | ≠0 | Hillside (saddle) | 5 |
| + | + | 0 | ≠0 | * | Hillside (convex) | 3 |
| + | + | * | 0 | * | Ravine | 9 |
| + | * | + | * | 0 | Ravine | 9 |
| + | + | + | ≠0 | ≠0 | Hillside (convex) | 3 |
| + | * | 0 | 0 | 0 | Cannot occur | — |

Topographic labels are divided into 2 subsets: (1) Those labels indicating that a strict, local, 1D extreme has occurred (peak, pit, ridge, ravine, and saddle) and (2) those labels not indicating that a strict, local, one-dimensional extreme has occurred (flat and hillside). It is not necessary to search the pixel's entire area for the zero crossing of the first directional derivative, but search only in the directions of extreme second directional derivatives, $\overline{\omega}_{(1)}$ and $\overline{\omega}_{(2)}$. This method can minimize the chance of overlooking an important topographic structure, since these directions are well aligned with curvature properties, and at the same time the computational cost becomes very small.

If $\lambda_1=\lambda_2\neq 0$, the directions $\overline{\omega}_{(1)}$ and $\overline{\omega}_{(2)}$ are not uniquely defined. In this case a zero crossing is searched for along the Newton direction, $H^{-1}\cdot\nabla f$, which points directly towards the extreme of a quadratic surface.

Once the first derivative maximum occurs, a zero crossing of the second directional derivative is searched for along the gradient direction. For a one-dimensional extreme, there are four cases to be considered: no zero crossing; one zero crossing; two zero crossings; and more than two crossings of the first directional derivative.

Case 1

If no zero crossing is found along either of the two extreme directions within the one-pixel area, then the pixel cannot be a local extreme and therefore must be assigned a label from the set (flat or hillside). The classification criteria are listed in Table 3.

TABLE 3

| $\|\nabla f\|$ | $\lambda_1$ | $\lambda_2$ | Topographic Categories | Labels |
|---|---|---|---|---|
| 0 | 0 | 0 | Flat | 1 |
| + | − | − | Concave hill | 4 |
| + | − | 0 | Concave hill | 4 |
| + | − | + | Saddle hill | 5 |
| + | 0 | 0 | Slope | 6 |
| + | + | − | Saddle hill | 5 |
| + | + | 0 | Convex hill | 3 |
| + | + | + | Convex hill | 3 |

Case 2

If a zero crossing of the first directional derivative is found within the one-pixel area, then the pixel is a strict, local and one-dimensional extreme and must be assigned a label from the set (peak, pit, ridge, ravine, or saddle). At the location of the zero crossing, the Hessian and gradient are recomputed. The classification criteria are applied as listed in Table 4.

TABLE 4

| $\|\nabla f\|$ | $\lambda_1$ | $\lambda_2$ | Topographic Categories | Labels |
|---|---|---|---|---|
| 0 | − | − | Peak | 8 |
| 0 | − | 0 | Ridge | 7 |
| 0 | − | + | Saddle | 2 |
| 0 | + | − | Saddle | 2 |
| 0 | + | 0 | Ravine | 9 |
| 0 | + | + | Pit | 10 |

Case 3

If there are two zero crossings of the first directional derivative, one in each direction of extreme curvature, then the Hessian and gradient must be recomputed at each zero crossing. Using the procedure just described, a label is assigned to each zero crossing. These labels are called Label 1 and Label 2. The final classification criteria are then based on the two labels as shown in Table 5.

TABLE 5

| Label 1 | Label 2 | Resulting final label |
|---|---|---|
| Peak (8) | Peak (8) | Peak (8) |
| Peak (8) | Ridge (7) | Peak (8) |
| Pit (10) | Pit (10) | Pit (10) |
| Pit (10) | Ravine (9) | Pit (10) |
| Saddle (2) | Saddle (2) | Saddle (2) |
| Ridge (7) | Ridge (7) | Ridge (7) |
| Ridge (7) | Ravine (9) | Saddle (2) |
| Ridge (7) | Saddle (2) | Saddle (2) |
| Ravine (9) | Ravine (9) | Ravine (9) |
| Ravine (9) | Saddle (2) | Saddle (2) |

Case 4

If more than two zero crossings occur within a one-pixel area, then in at least one of the extreme directions there are at least two zero crossings. Once this happens, the zero crossing closest to the one-pixel center is chosen and the others are ignored. With this approximation this case becomes identical to Case 3.

In summary, at each pixel of the image, the following four steps need to be performed:

1. Calculate the fitting coefficients, $k_1$ through $k_{10}$, of a two-dimensional cubic polynomial in a ws×ws neighborhood around the pixel, as explained in section 3.1.3;
2. Compute the gradient, the gradient magnitude, and the eigenvalues and eigenvectors of the Hessian matrix at the center (0,0) of the pixel's neighborhood;
3. Search in the direction of the eigenvectors for a zero crossing of the first directional derivative within the one-pixel area. If the eigenvalues of H are equal and nonzero, then search in the Newton direction;
4. Recompute the gradient, the gradient magnitude, and the values of second directional derivative extremes at each zero crossing of the first directional derivative. Then apply the labeling method.

Take an image with four up-down Gaussian peak-pits as an example for topographic labeling.

As mentioned earlier, that '0' in the above tables actually means "not significantly different from zero". In the practical program some threshold values need to be set up to define positive, zero and negative values. Different thresholds are set for the values of gradient magnitude $\|\nabla f\|$ (grad_thr), eigenvalues $\lambda_{11,2}$ (eig_thr), dot product $\nabla f \cdot \overline{\omega}_{(1,2)}$ (dotp_thr) and general values (abs_thr), respectively. The threshold values are used to determine if either of the relevant parameters is essentially zero. For example, eig_thr is used as:

if $|\lambda| \leq $ eig_th| then $\lambda=0$;
if $\lambda>$eig_thr then $\lambda>0$
if $\lambda<−$eig_thr then $\lambda<0$.

Figure 9:
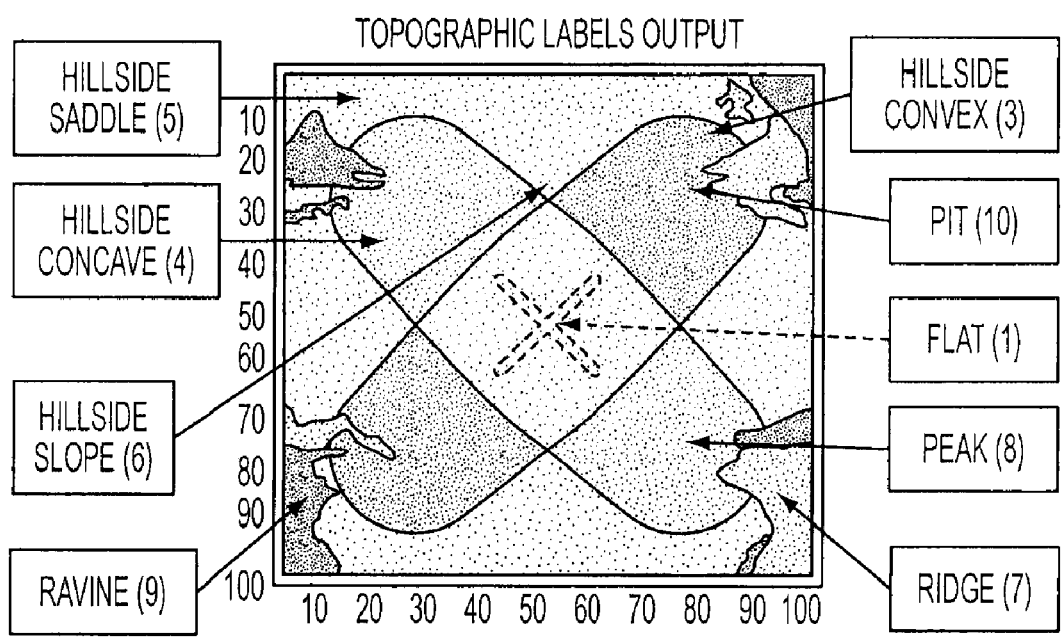
FIG. 9 shows labeling with different threshold values.

The topographic labels are very sensitive to these threshold values. With the following threshold values: grad_thr=0.01, eig_thr=0.01, dotp_thr=0.01, abs_thr=0.01, and ws=5, the labeling result of the four Gaussian peak-pits is shown in FIG. 9.

Figure 10:
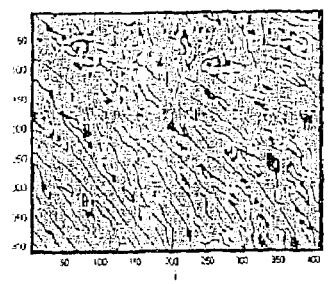
FIG. 10 shows labeling results of the different images for all 6 replicas.
Figure 10:
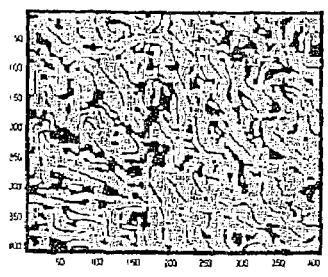
Figure 10:
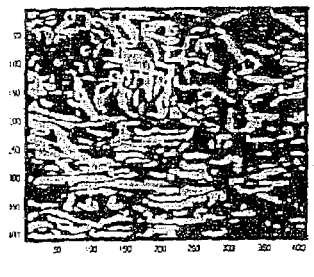
Figure 10:
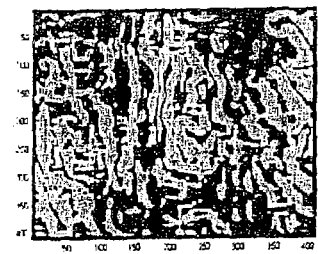
Figure 10:
Figure 10:

When the threshold values are set as: grad_thr=0.25, eig_thr=0.5, dotp _thr=0.5, and abs_thr=0.01, and the facet model window size is 15, ws=15, the topographic labels are obtained (shown in FIG. 10) for the difference images of all replicas after the operation of pixel subtraction as mentioned previously. FIG. 10 indicates that the labeling results obviously reveal some information related to the wrinkle degrees of the six replicas.

Based on the labeling method, it is not certain how to decide what labels account for the degree of wrinkles in the fabrics or replicas, though topographically labeled images such as those shown in FIG. 10 obviously contain information about these wrinkles. From the labeling of the Gaussian peak-pits image shown in FIG. 9, it is also not clear which labels can be used to characterize wrinkle degrees.

Figure 11:
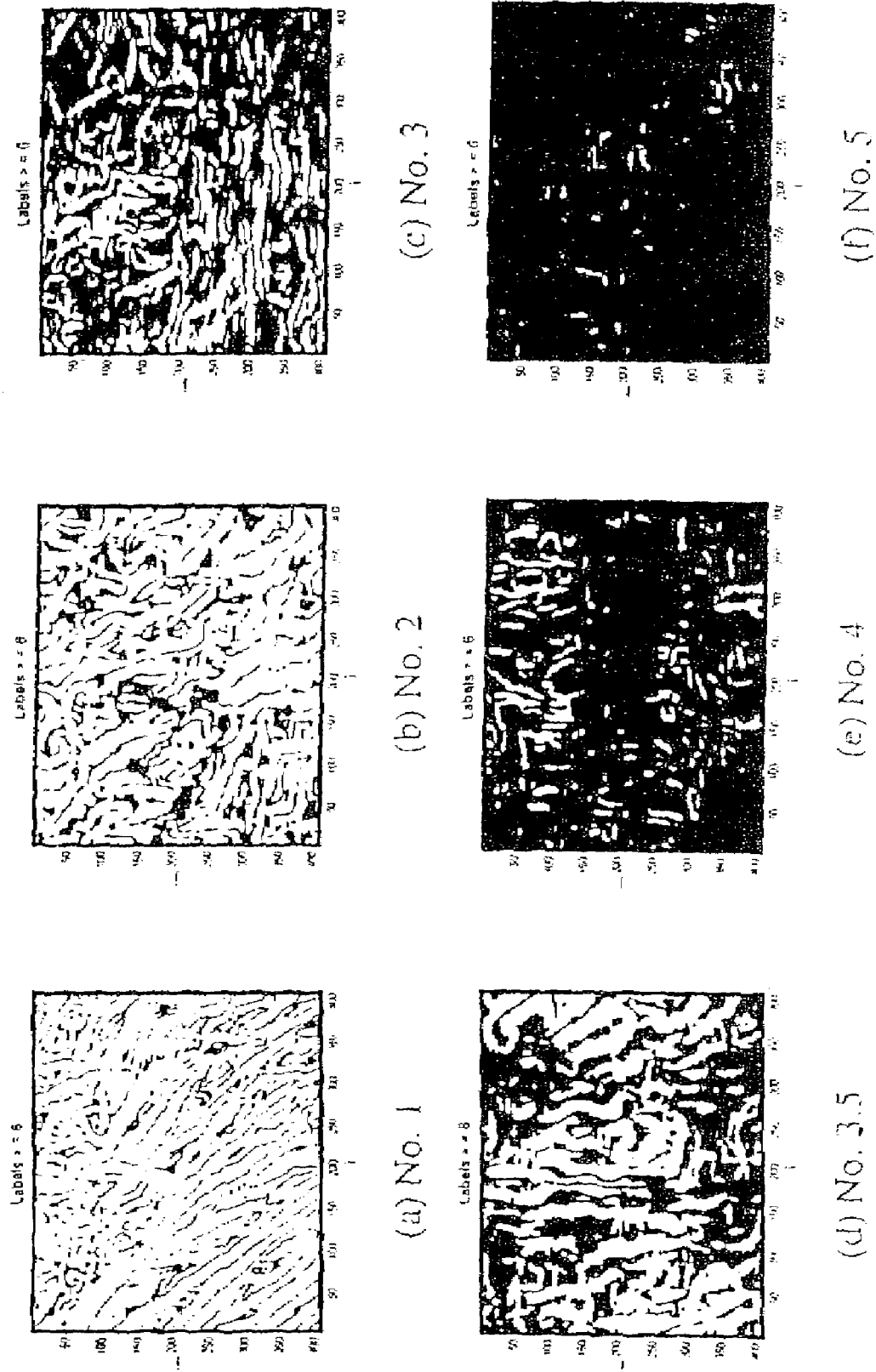
FIG. 11 shows binary images of labels $\geq 6$ resulted from FIG. 10.

In this project, those labels equal to 6 or greater than 6 are experimentally chosen and the pixel areas of these labels are summed up to indicate wrinkling degrees. These pixels include pits, ravines, peaks, ridges and hillside slopes. The binary images of the labels $\geq 6$ resulting from FIG. 10 are shown in FIG. 11. The percentage (denoted by $\Theta$) of labels $\geq 6$ over the entire image (excluding the boundary areas) is calculated and is used as the feature for evaluating the wrinkles, So far, the facet model algorithm has been described step by step. With $\Theta$ to indicate wrinkling degrees in replicas and fabrics, experimental results will be presented.

Plane-Cutting Algorithm

Figure 12:
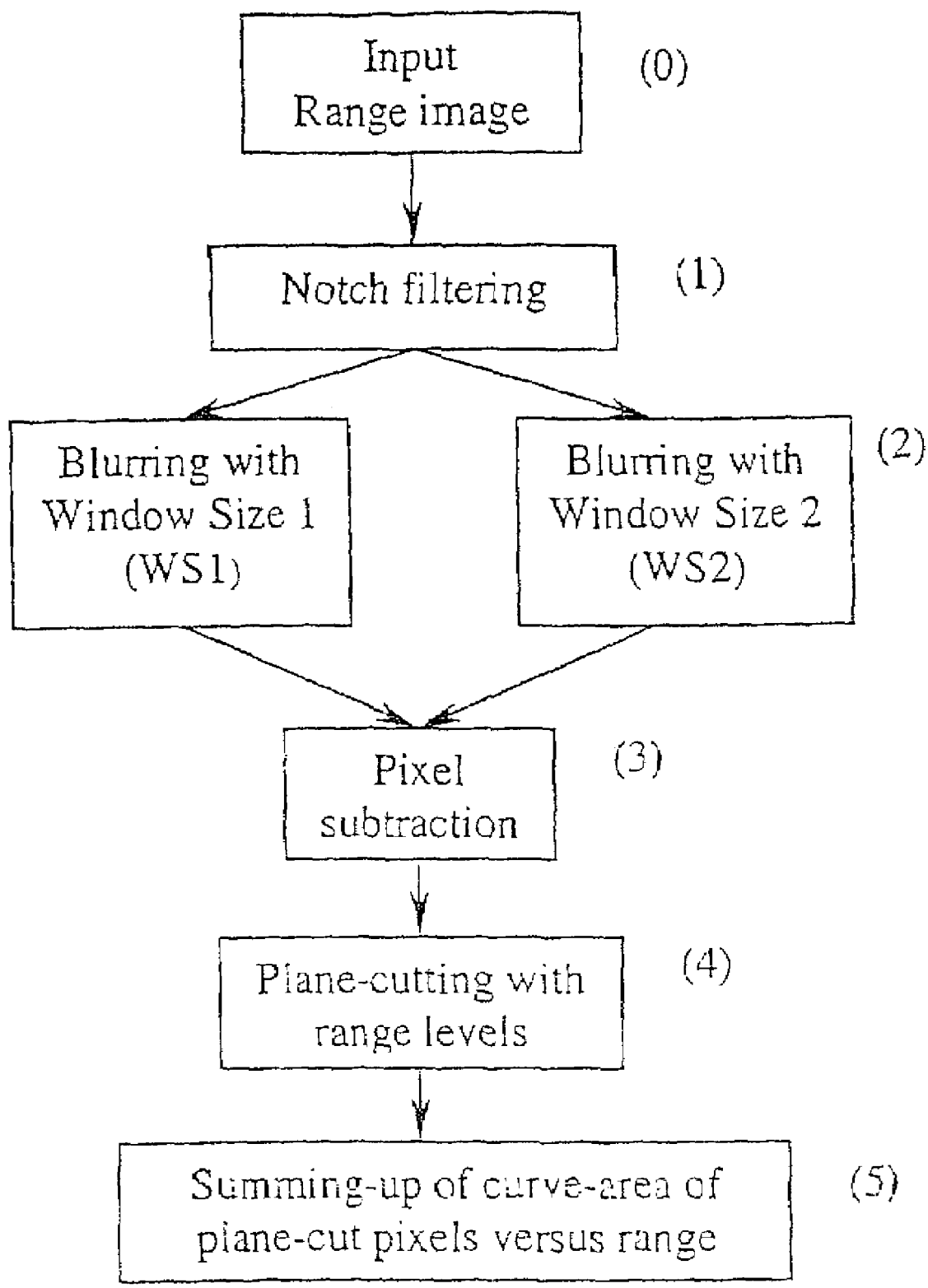
FIG. 12 is a flow chart of the plane-cutting algorithm.

The plane-cutting algorithm is developed from the facet model algorithm. It is much simpler than the facet model algorithm, since the plane-cutting algorithm has lower mathematical calculations. This algorithm is illustrated in the following flow chart (FIG. 12).

Before the step (4), the steps executed are completely the same as those introduced in the facet model algorithm The input image (the original range image) is processed by a notch filter, by blurring with different window sizes, and then by pixel subtraction. These steps are used to enhance wrinkles in the original range image. After that, the plane-cutting operation at range levels is performed to construct a curve of plane-cut pixel percentages versus range levels. Then the area enclosed by the axes of plane-cut pixel percentages range levels and the curve, is calculated to characterize the degree of wrinkles.

Figure 13:
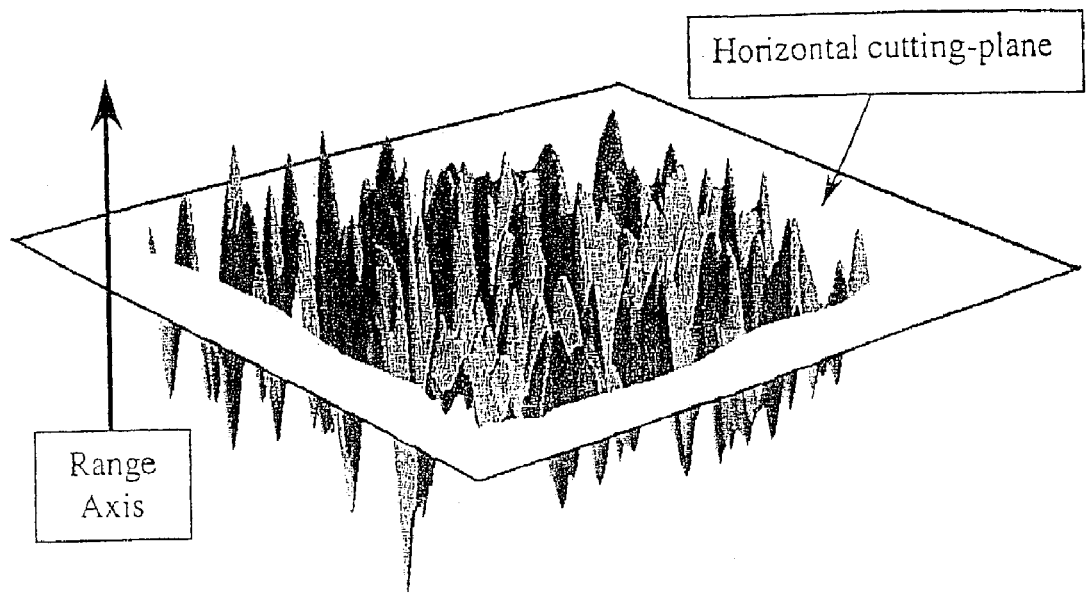
FIG. 13 is a sketch plot of the plane-cutting algorithm.

After the difference image is obtained from the subtraction, it is processed by plane-cutting. FIG. 13 shows how the plane-cutting operation at a range level works.

Figure 14:
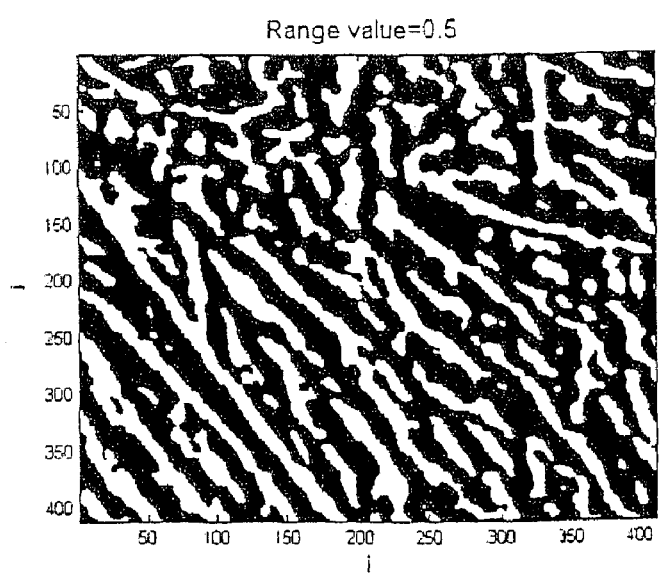
FIG. 14 shows the sample intersected area between the cutting-plane and the range image.
Figure 15:
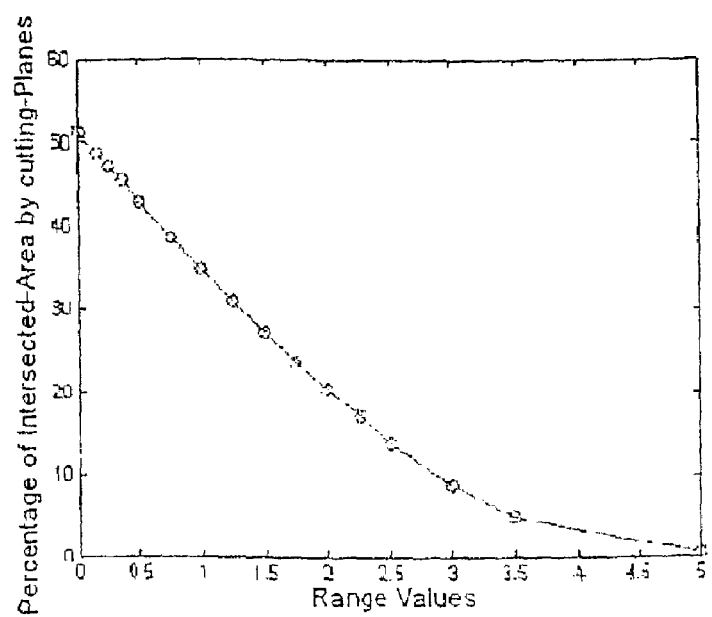
FIG. 15 is a sample curve of plane-cut pixels (percentage) versus range levels.

In FIG. 13, the horizontal cutting-plane at a certain range level is perpendicular to the range axis. The cutting-plane is parallel to the image plane constructed by the row and column axes. From the cutting plane and the range image, an intersected area is easily found as shown in FIG. 14. This image shows the total pixels at that range level of the difference image from the previous step. With a series of cutting-planes at different range levels, a curve of plane-cut pixels (percentage over the whole image) versus range levels is obtained (FIG. 15). The curve reveals some information of wrinkling.

Figure 16:
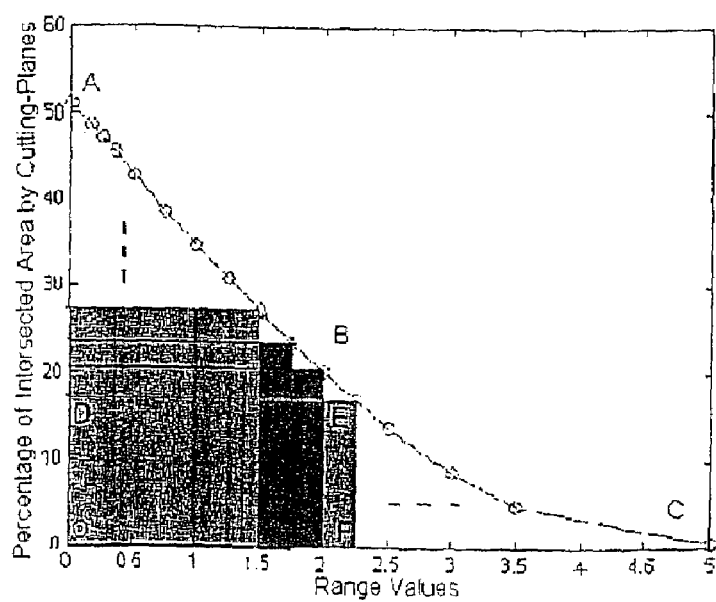
FIG. 16 shows an alternate method of calculation the area OABC.

In order to conveniently and numerically represent the wrinkling degrees based on the curves of plane-cut pixels versus range levels, the areas, enclosed by the axes of plane-cut pixels, range levels and the curves, are calculated to characterize the degrees of wrinkles. The larger the area, the more seriously the wrinkling. Alternatively, the areas of this enclosing are calculated as shown in FIG. 16. Instead of calculating the area of OABC, all the areas of rectangles (for example ODEF is one rectangle) are summed up while these rectangles are constructed to make each data point and the origin as their diagonal points. This area sum is symbolically denoted as $\Omega$. Later the natural logarithm of $\Omega$, log($\Omega$), is used to magnify tiny differences. That is, in the plane-cutting algorithm log($\Omega$) is the feature used for evaluating degrees of wrinkling.

The plane-cutting algorithm is relatively simple to apply, since the facet-model algorithm is related to mathematical calculations. The applications of both algorithms will be shown in the next chapter. In summary, the wrinkle-evaluation is simplified to be the following steps:

1. Capturing range images of replicas and fabrics;
2. Calculating the values of $\Theta$ in the facet model algorithm or log($\Omega$) in the plane-cutting algorithm;
3. Classifying the replicas and fabric specimens by $\Theta$ or log($\Omega$);
4. Comparing with classified replicas by wrinkling degrees originally labeled, and checking whether the two classifications are matched or not;
5. Comparing with classified fabric specimens by wrinkle grades from technicians, and checking whether the two classifications are matched or not.

Experimental Results

There are 42 fabric specimens used to evaluate wrinkles. Before they were delivered to use with the laser camera system, each of them had been evaluated twice by three technicians. The purpose of this is to take an average grade for the degree of wrinkling of each fabric. Table 6 shows the detailed grades from the three technicians. The first and second columns are the sample order and the sample ID. The third and fourth columns are grades evaluated twice by the first technician. The interval between the twice evaluation is one week. The fifth and sixth columns are grades by the second technician. The seventh and eighth columns are grades by the third technician. The ninth column is the averages of the grades by all three technicians. The last column is the final grades rounded-up from the ninth column.

From Table 6, it is obvious that a fabric specimen might have different grades when evaluated by different technicians, and even when evaluated at different times by the same technician. There are quite a few reasons for this phenomenon. Besides the reasons of subjectivity mentioned above, the wrinkles might have been more or less altered during the evaluation process. For example, the sample 3a was graded as No. 3 (average) by technicians. The wrinkles of the sample 3a shown in the range image have been altered so as to be No. 1 or No. 2, and this sample is discarded.

TABLE 6

| Sample Order | Sample ID | Tech1 First | Tech1 Second | Tech2 First | Tech2 Second | Tech3 First | Tech3 Second | Average all | Final degree |
|---|---|---|---|---|---|---|---|---|---|
| 1 | 1TT | 3 | 3 | 2 | 3 | 3 | 3 | 2.8333 | 3 |
| 2 | 2TT | 2 | 2 | 2 | 2 | 2 | 2 | 2 | 2 |
| 3 | 3TT | 3 | 3 | 3 | 3 | 3 | 3.5 | 3.0833 | 3 |
| 4 | 4TT | 3 | 3 | 3 | 3 | 3 | 2 | 2.8333 | 3 |
| 5 | 5TT | 1 | 1 | 1 | 2 | 2 | 2 | 1.5 | 1 |
| 6 | 6TT b | 5 | 5 | 5 | 5 | 5 | 4 | 4.8333 | 5 |
| 7 | 7TT | 3 | 3 | 3 | 3 | 3 | 3 | 3 | 3 |
| 8 | 8TT | 2 | 2 | 2 | 1 | 2 | 2 | 1.8333 | 2 |
| 9 | 9TT a | 4 | 4 | 3 | 3.5 | 3.5 | 3.5 | 3.5833 | 3.5 |
| 10 | 10TT | 1 | 1 | 2 | 1 | 3 | 1 | 1.5 | 1 |
| 11 | 11TT b | 5 | 5 | 5 | 5 | 5 | 3.5 | 4.75 | 5 |
| 12 | 12TT | 1 | 1 | 1 | 1 | 2 | 1 | 1.1667 | 1 |
| 13 | 13TT a | 4 | 4 | 3 | 3.5 | 3 | 3 | 3.4167 | 3.5 |
| 14 | 14TT b | 5 | 5 | 5 | 5 | 5 | 4 | 4.8333 | 5 |
| 15 | 15TT | 3 | 3 | 3 | 3 | 3 | 3 | 3 | 3 |
| 16 | 16TT | 2 | 3 | 2 | 2 | 2 | 3 | 2.3333 | 2 |
| 17 | 17TT | 3 | 3.5 | 3 | 3 | 3 | 3 | 3.0833 | 3 |
| 18 | 18TT a | 4 | 4 | 3.5 | 3.5 | 3 | 3 | 3.5 | 3.5 |
| 19 | 1 a | 3.5 | 4 | 3.5 | 4 | 3 | 3.5 | 3.5833 | 3.5 |
| 20 | 2 a | 3.5 | 3 | 3.5 | 4 | 3 | 3.5 | 3.4167 | 3.5 |
| X | 3 a | 4 | 2 | 4 | 3.5 | 3 | 3 | 3.25 | 3 |
| 21 | 4 a | 4 | 3.5 | 3.5 | 3.5 | 3.5 | 3.5 | 3.5833 | 3.5 |
| 22 | 5 a | 4 | 3.5 | 3.5 | 3.5 | 4 | 3 | 3.5833 | 3.5 |
| 23 | 6 a | 3.5 | 3.5 | 4 | 3.5 | 4 | 3.5 | 3.6667 | 3.5 |
| 24 | 7 a | 3.5 | 3 | 3 | 3 | 3 | 3 | 3.0833 | 3 |

TABLE 6-continued

| Sample Order | Sample ID | Tech1 First | Tech1 Second | Tech2 First | Tech2 Second | Tech3 First | Tech3 Second | Average all | Final degree |
|---|---|---|---|---|---|---|---|---|---|
| 25 | 8 a | 4 | 3 | 3.5 | 3 | 3.5 | 3 | 3.3333 | 3 |
| 26 | 1 b | 5 | 5 | 5 | 4 | 5 | 3.5 | 4.5833 | 5 |
| 27 | 2 b | 5 | 5 | 5 | 5 | 5 | 4 | 4.8333 | 5 |
| 28 | 3 b | 5 | 5 | 4 | 4 | 4 | 3.5 | 4.25 | 4 |
| 29 | 4 b | 5 | 4 | 4 | 4 | 4 | 3.5 | 4.0833 | 4 |
| 30 | 5 b | 5 | 5 | 5 | 5 | 5 | 4 | 4.8333 | 5 |
| 31 | 6 b | 5 | 5 | 5 | 5 | 5 | 3.5 | 4.75 | 5 |
| 32 | 7 b | 4 | 5 | 4 | 4 | 3.5 | 3.5 | 4 | 4 |
| 33 | 8 b | 5 | 4 | 4 | 4 | 4 | 3 | 4 | 4 |
| 34 | 1 c | 4 | 3 | 3.5 | 3.5 | 3.5 | 3 | 3.4167 | 3.5 |
| 35 | 2 c | 3.5 | 3 | 4 | 4 | 3.5 | 3.5 | 3.5833 | 3.5 |
| 36 | 3 c | 3 | 3 | 3 | 3 | 3 | 3 | 3 | 3 |
| 37 | 4 c | 2 | 2 | 3 | 2 | 2 | 2 | 2.1667 | 2 |
| 38 | 5 c | 4 | 4 | 4 | 4 | 4 | 3.5 | 3.9167 | 4 |
| 39 | 6 c | 3 | 3.5 | 3 | 3 | 3 | 2 | 2.9167 | 3 |
| 40 | 7 c | 3 | 3 | 3 | 3 | 3 | 3 | 3 | 3 |
| 41 | 8 c | 4 | 3.5 | 3 | 3 | 3.5 | 3 | 3.3333 | 3 |

Figure 17:
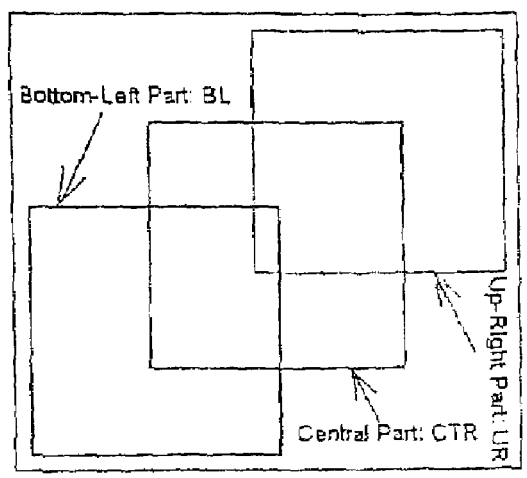
FIG. 17 is a sketch map of three parts for replicas.

Now the algorithms discussed in the previous section are used to extract the feature values, $\Theta$ and $\log(\Omega)$, from the range images. These range images of all fabric specimens are captured around the central parts of the fabrics, avoiding the hemmed boundary interferences. The 6 replicas mentioned above are graded as 1, 2, 3, 3.5, 4 and 5. For each replica, three images are captured by the laser camera system and they are located on the central (CTR), bottom-left (BL) and upper-right (UR) positions. It is noted that the three parts overlap and a sketch map of them is depicted in FIG. 17.

Figure 18:
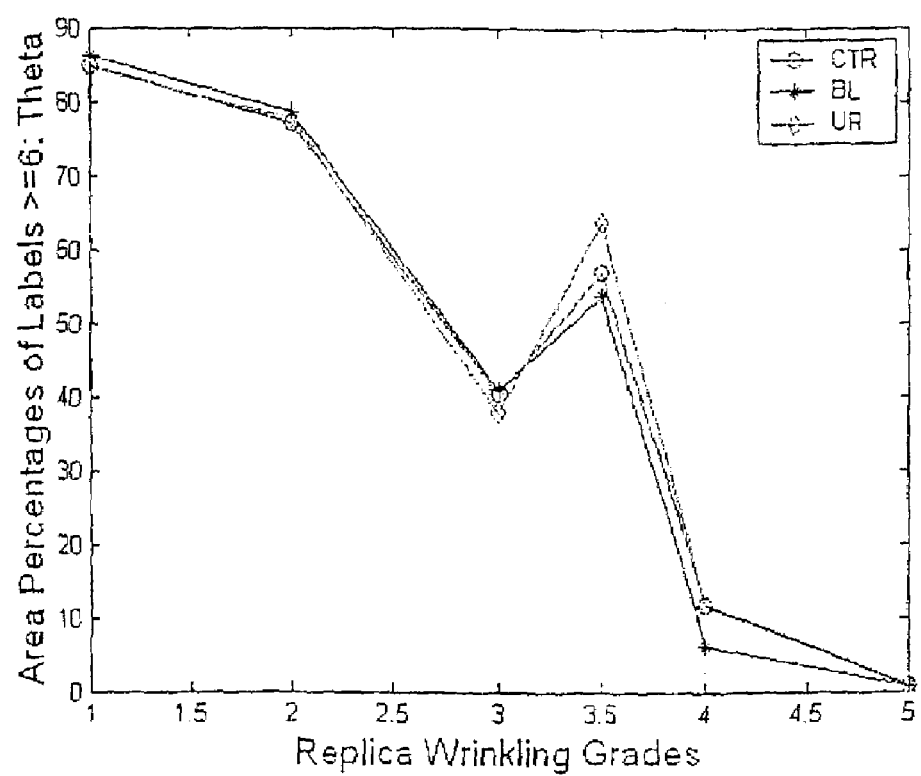
FIG. 18 shows curves of Θ versus wrinkle grade for all six replicas with WS1=91, WS2=11 and ws=15 (CTR—Central, BL—Bottom left, UR—Upper right)

When the parameters used in the facet model algorithm are as follows:

Blurring window sizes: WS1=91, WS2=11,

Facet model window size: ws=15,

Threshold values: grad_thr=0.175, eig_thr=0.5, dotp_thr=0.5, abs_thr=0.01,

FIG. 18 shows the curves of $\Theta$ versus wrinkle grades for all six replicas. We call these $\Theta$ as $\Theta(91/11/15)$, expressing the blurring window sizes and the facet model window size. The horizontal axis is the levels of replicas: 1, 2, 3, 3.5, 4, and 5, and the vertical axis is the $\Theta$ values of all replicas ranging from almost 0 to 85%. It is observed that the three parts of each replica are clustered together through their values of $\Theta$. The six replicas show substantial differences from each other. The values of $\Theta$ are decreased with the increase of the wrinkling grade values, except for the No. 3 replica since it contains a different type of wrinkle: creases.

It is noted that the results obtained above depend on the parameters such as the blurring window sizes, the facet model window size, threshold values, and the notch filter window size as well. According to the properties of the creases, different window sizes of blurring and the facet model are applied as follows:

Blurring window sizes: WS1=15, WS2=5;

Facet model window size: ws=11.

Figure 4:
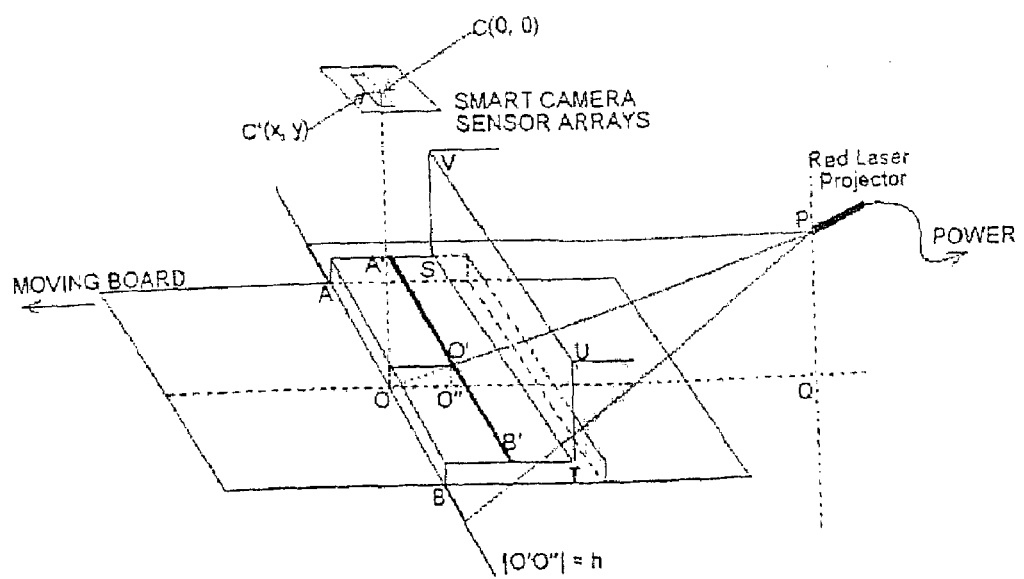
FIG. 4 is an illustration of blocking or occlusion.
Figure 19:
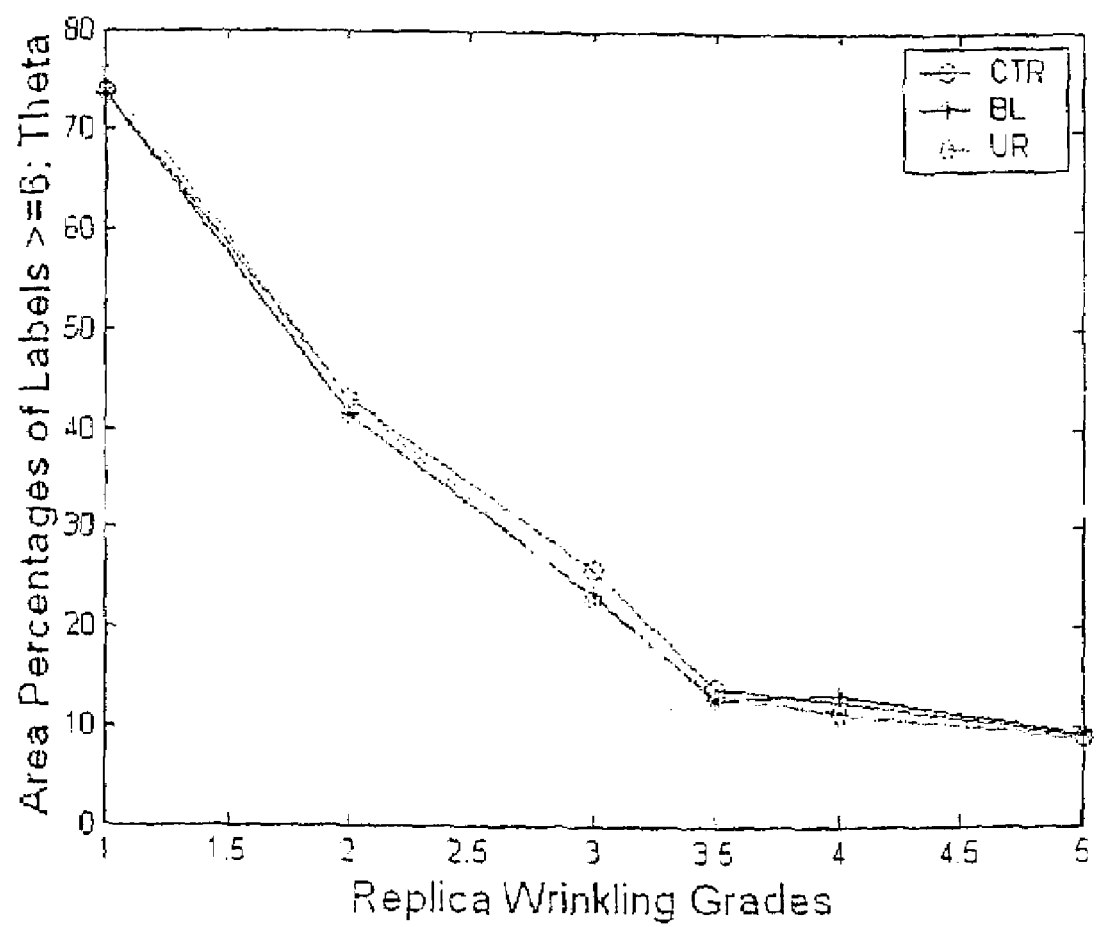
FIG. 19 shows curves of Θ versus wrinkle grades for all six replicas with WS1=15, WS2=5, and ws=11 (CTR—Central; BL—Bottom left; UP—Upper right)

When the other parameters are kept the same, the curves of $\Theta$ versus wrinkle grades for all six replicas are plotted in FIG. 19. We call these $\Theta$ as $\Theta(15/05/11)$. With the smaller blurring window sizes, the values $\Theta$ of all replicas are able to separate the replicas except between the No. 5, No. 4, and No. 3.5 replicas. However, much difference between the No. 3 and No. 3.5 has been obtained. Therefore, as shown in FIG. 4.3, the replicas can be classified into 5 categories: No. 1, No. 2, No. 3 and No. 3.5 together, No. 4, and No. 5. Then according to the difference between the No. 3 and No 3.5 replicas shown in FIG. 4.4, the No. 3 and No. 3.5 replicas can be separated into two categories. In the next section this difference is used to classify the fabrics between No. 3 and No. 3.5.

Figure 20:
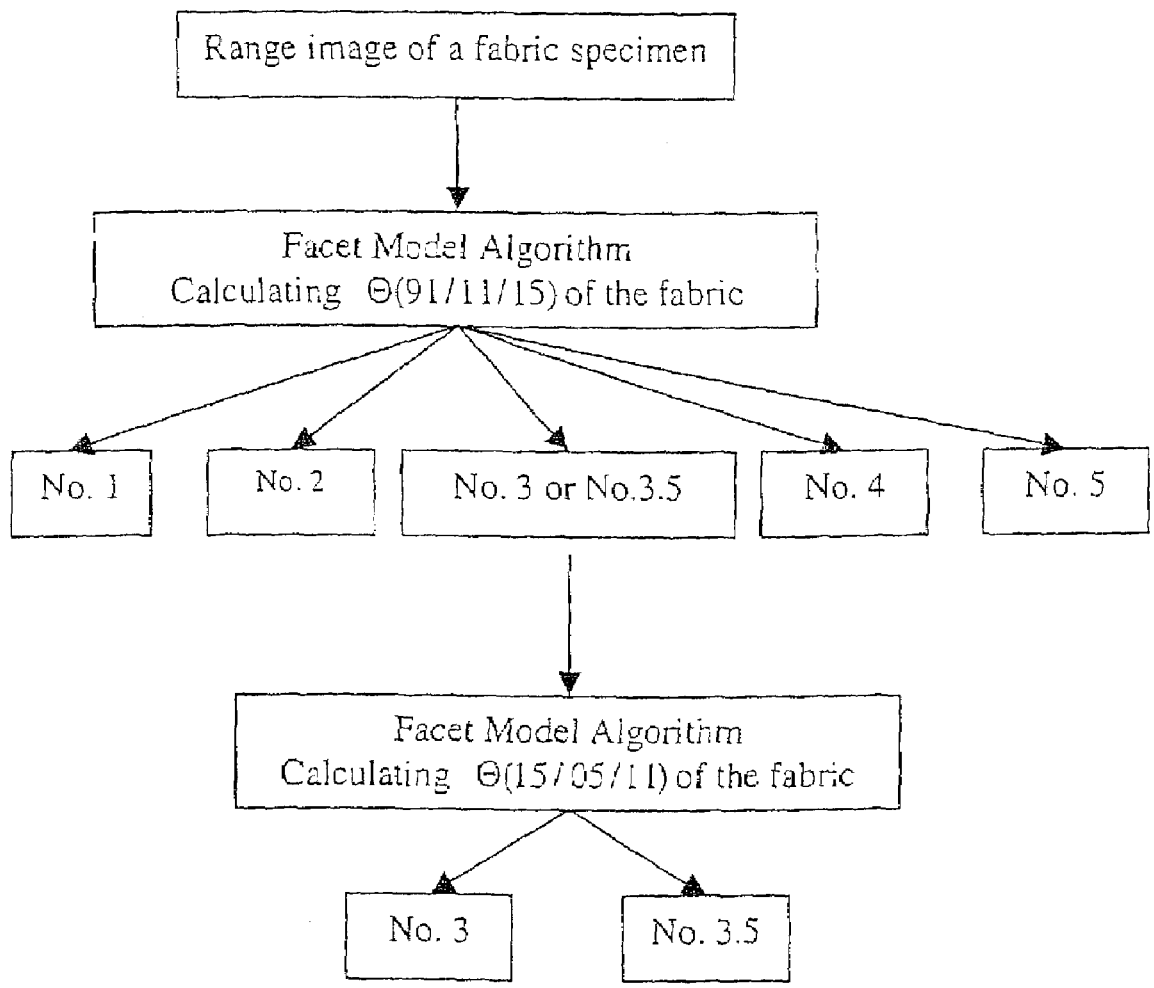
FIG. 20 is a flow chart indicating the application procedure of the facet model algorithm.

According to the results of replicas shown in above, the application procedure for the fabric specimens is indicated in the following flow chart FIG. 20. Once the value of $\Theta(91/11/15)$ or $\Theta(15/05/11)$ of a fabric specimen is calculated, it is compared to the corresponding average values of each replica, and the fabric is then graded the same as a replica which has the most similar value of $\Theta$. The grades of all fabric specimens are shown in Table 7.

From Table 7, it is observed that the grades from the facet model algorithm are not completely consistent with the grades by the technicians, and the correlation coefficient between them is about 88.5%. Comparing the two kinds of wrinkle grades, the mismatch occurs in the way the grade values from the facet model algorithm are often

TABLE 7

| Sample ID | Tech1 First | Tech1 Second | Tech2 First | Tech2 Second | Tech3 First | Tech3 Second | Average all | Final grades | Facet Model grades | Correl. Coeff. |
|---|---|---|---|---|---|---|---|---|---|---|
| 1TT | 3 | 3 | 2 | 3 | 3 | 3 | 2.83333 | 3 | 2 | 0.88458052 |
| 2TT | 2 | 2 | 2 | 2 | 2 | 2 | 2 | 2 | 1 | |
| 3TT | 3 | 3 | 3 | 3 | 3 | 3.5 | 3.08333 | 3 | 2 | |
| 4TT | 3 | 3 | 3 | 3 | 3 | 2 | 2.83333 | 3 | 2 | |
| 5TT | 1 | 1 | 1 | 2 | 2 | 2 | 1.5 | 1 | 1 | |
| 6TT b | 5 | 5 | 5 | 5 | 5 | 4 | 4.83333 | 5 | 4 | |
| 7TT | 3 | 3 | 3 | 3 | 3 | 3 | 3 | 3 | 2 | |
| 8TT | 2 | 2 | 2 | 1 | 2 | 2 | 1.83333 | 2 | 1 | |

TABLE 7-continued

| Sample ID | Tech1 First | Tech1 Second | Tech2 First | Tech2 Second | Tech3 First | Tech3 Second | Average all | Final grades | Facet Model grades | Correl. Coeff. |
|---|---|---|---|---|---|---|---|---|---|---|
| 9TT a | 4 | 4 | 3 | 3.5 | 3.5 | 3.5 | 3.58333 | 3.5 | 3.5 | |
| 10TT | 1 | 1 | 2 | 1 | 3 | 1 | 1.5 | 1 | 1 | |
| 11TT b | 5 | 5 | 5 | 5 | 5 | 3.5 | 4.75 | 5 | 4 | |
| 12TT | 1 | 1 | 1 | 1 | 2 | 1 | 1.16667 | 1 | 1 | |
| 13TT a | 4 | 4 | 3 | 3.5 | 3 | 3 | 3.41667 | 3.5 | 3.5 | |
| 14TT b | 5 | 5 | 5 | 5 | 5 | 4 | 4.83333 | 5 | 3.5 | |
| 15TT | 3 | 3 | 3 | 3 | 3 | 3 | 3 | 3 | 2 | |
| 16TT | 2 | 3 | 2 | 2 | 2 | 3 | 2.33333 | 2 | 1 | |
| 17TT | 3 | 3.5 | 3 | 3 | 3 | 3 | 3.08333 | 3 | 2 | |
| 18TT a | 4 | 4 | 3.5 | 3.5 | 3 | 3 | 3.5 | 3.5 | 3.5 | |
| 1 a | 3.5 | 4 | 3.5 | 4 | 3 | 3.5 | 3.58333 | 3.5 | 3.5 | |
| 2 a | 3.5 | 3 | 3.5 | 4 | 3 | 3.5 | 3.41667 | 3.5 | 2 | |
| 4 a | 4 | 3.5 | 3.5 | 3.5 | 3.5 | 3.5 | 3.58333 | 3.5 | 3.5 | |
| 5 a | 4 | 3.5 | 3.5 | 3.5 | 4 | 3 | 3.58333 | 3.5 | 3 | |
| 6 a | 3.5 | 3.5 | 4 | 3.5 | 4 | 3.5 | 3.66667 | 3.5 | 3 | |
| 7 a | 3.5 | 3 | 3 | 3 | 3 | 3 | 3.08333 | 3 | 2 | |
| 8 a | 4 | 3 | 3.5 | 3 | 3.5 | 3 | 3.33333 | 3 | 1 | |
| 1 b | 5 | 5 | 5 | 4 | 5 | 3.5 | 4.58333 | 5 | 3.5 | |
| 2 b | 5 | 5 | 5 | 5 | 5 | 4 | 4.83333 | 5 | 3.5 | |
| 3 b | 5 | 5 | 4 | 4 | 4 | 3.5 | 4.25 | 4 | 3.5 | |
| 4 b | 5 | 4 | 4 | 4 | 4 | 3.5 | 4.08333 | 4 | 3.5 | |
| 5 b | 5 | 5 | 5 | 5 | 5 | 4 | 4.83333 | 5 | 4 | |
| 6 b | 5 | 5 | 5 | 5 | 5 | 3.5 | 4.75 | 5 | 4 | |
| 7 b | 4 | 5 | 4 | 4 | 3.5 | 3.5 | 4 | 4 | 3.5 | |
| 8 b | 5 | 4 | 4 | 4 | 4 | 3 | 4 | 4 | 3.5 | |
| 1 c | 4 | 3 | 3.5 | 3.5 | 3.5 | 3 | 3.41667 | 3.5 | 3 | |
| 2 c | 3.5 | 3 | 4 | 4 | 3.5 | 3.5 | 3.58333 | 3.5 | 2 | |
| 3 c | 3 | 3 | 3 | 3 | 3 | 3 | 3 | 3 | 2 | |
| 4 c | 2 | 2 | 3 | 2 | 2 | 2 | 2.16667 | 2 | 1 | |
| 5 c | 4 | 4 | 4 | 4 | 4 | 3.5 | 3.91667 | 4 | 3 | |
| 6 c | 3 | 3.5 | 3 | 3 | 3 | 2 | 2.91667 | 3 | 2 | |
| 7 c | 3 | 3 | 3 | 3 | 3 | 3 | 3 | 3 | 2 | |
| 8 c | 4 | 3.5 | 3 | 3 | 3.5 | 3 | 3.33333 | 3 | 2 | | less than the grades by technicians. It is also observed that there is no grade of No. 5 while using the facet model algorithm. The reason accounting for this might be the surface properties of the fabric specimens: they are hairy surfaces.

The parameters used in the plane-cutting algorithm are listed below:

Blurring window sizes: WS1=9, WS2=5.

Figure 21:
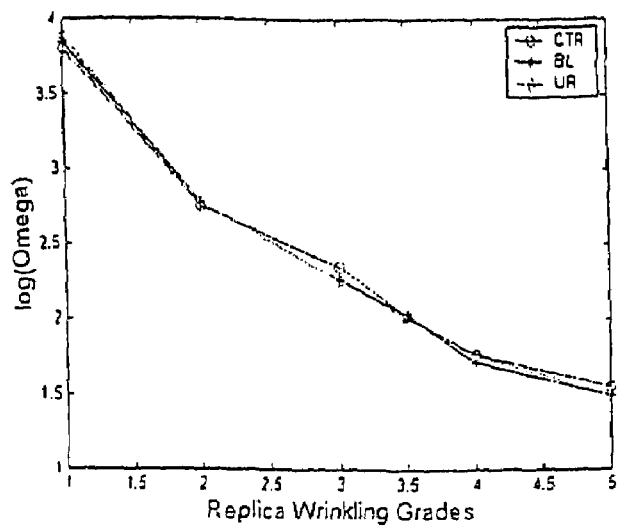
FIG. 21 show curves of $\log(\Omega)$ versus wrinkle grades for all six replicas with blurring window sizes: WS1=9, WS2=5 (CTR—Central; BL—Bottom Left; UP—Upper right)

FIG. 21 shows the curves of log($\Omega$) versus wrinkle grades for all six replicas. We call these values of log($\Omega$)(9/5) due to the blurring window sizes. The horizontal axis is the wrinkle levels of replicas: 1, 2, 3, 3.5, 4, and 5, and the vertical axis is the log($\Omega$) values ranging from 1.5 to 4. The three parts of each replica are clustered together. These curves show that the plane-cutting algorithm separates the 6 replicas, especially the No. 3 replica with creases. It is noted that the blurring window sizes are chosen to WS1=9 and WS2=5 in order to highlight these crease-shaped wrinkles. This point will be clearer after more discussion.

Figure 22:
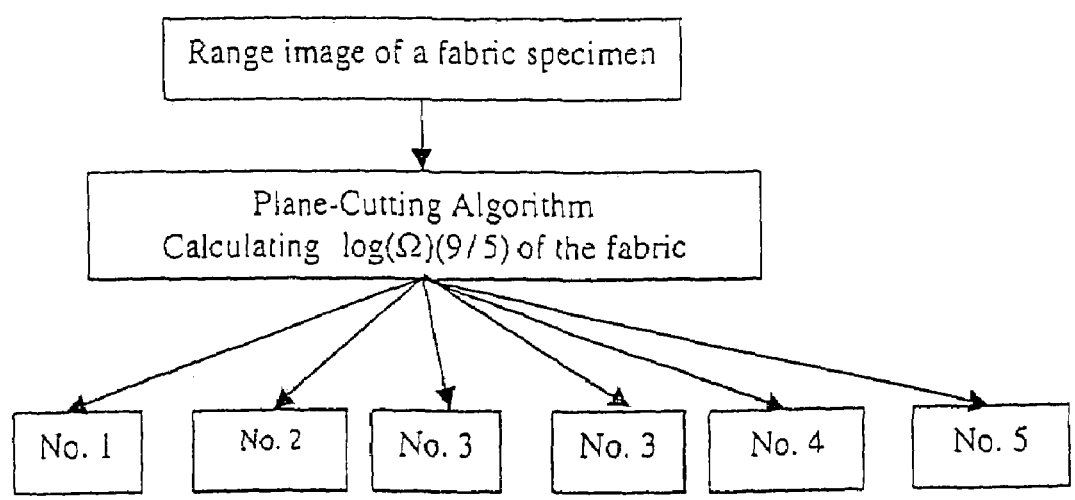
FIG. 22 is a flow chart indicating the application procedure of the plane-cutting algorithm.

According to the results of replicas shown, the application procedure for the fabric specimens is indicated FIG. 22.

After the value of log($\Omega$)(9/5) for each fabric is calculated, it is compared to the corresponding value of each replica, and classified to a relevant grade of that replica with the close value of log($\Omega$)(9/5). The grades of all fabric specimens from the plane-cutting algorithm are listed in Table 8.

TABLE 8

| Sample ID | Tech1 First | Tech1 Second | Tech2 First | Tech2 Second | Tech3 First | Tech3 Second | Average all | Final grades | P-Cutting grades | Correl. Coeff. |
|---|---|---|---|---|---|---|---|---|---|---|
| 1TT | 3 | 3 | 2 | 3 | 3 | 3 | 2.83333 | 3 | 3 | 74.50% |
| 2TT | 2 | 2 | 2 | 2 | 2 | 2 | 2 | 2 | 2 | |
| 3TT | 3 | 3 | 3 | 3 | 3 | 3.5 | 3.08333 | 3 | 3 | |
| 4TT | 3 | 3 | 3 | 3 | 3 | 2 | 2.83333 | 3 | 3 | |
| 5TT | 1 | 1 | 1 | 2 | 2 | 2 | 1.5 | 1 | 1 | |
| 6TT b | 5 | 5 | 5 | 5 | 5 | 4 | 4.83333 | 5 | 5 | |
| 7TT | 3 | 3 | 3 | 3 | 3 | 3 | 3 | 3 | 3 | |
| 8TT | 2 | 2 | 2 | 1 | 2 | 2 | 1.83333 | 2 | 1 | |
| 9TT a | 4 | 4 | 3 | 3.5 | 3.5 | 3.5 | 3.58333 | 3.5 | 4 | |
| 10TT | 1 | 1 | 2 | 1 | 3 | 1 | 1.5 | 1 | 1 | |
| 11TT b | 5 | 5 | 5 | 5 | 5 | 3.5 | 4.75 | 5 | 5 | |
| 12TT | 1 | 1 | 1 | 1 | 2 | 1 | 1.16667 | 1 | 1 | |
| 13TT a | 4 | 4 | 3 | 3.5 | 3 | 3 | 3.41667 | 3.5 | 5 | |
| 14TT b | 5 | 5 | 5 | 5 | 5 | 4 | 4.83333 | 5 | 5 | |
| 15TT | 3 | 3 | 3 | 3 | 3 | 3 | 3 | 3 | 3 | |
| 16TT | 2 | 3 | 2 | 2 | 2 | 3 | 2.33333 | 2 | 1 | |

TABLE 8-continued

| Sample ID | Tech1 First | Tech1 Second | Tech2 First | Tech2 Second | Tech3 First | Tech3 Second | Average all | Final grades | P-Cutting grades | Correl. Coeff. |
|---|---|---|---|---|---|---|---|---|---|---|
| 17TT | 3 | 3.5 | 3 | 3 | 3 | 3 | 3.08333 | 3 | 2 | |
| 18TT a | 4 | 4 | 3.5 | 3.5 | 3 | 3 | 3.5 | 3.5 | 4 | |
| 1 a | 3.5 | 4 | 3.5 | 4 | 3 | 3.5 | 3.58333 | 3.5 | 4 | |
| 2 a | 3.5 | 3 | 3.5 | 4 | 3 | 3.5 | 3.41667 | 3.5 | 2 | |
| 4 a | 4 | 3.5 | 3.5 | 3.5 | 3.5 | 3.5 | 3.58333 | 3.5 | 3 | |
| 5 a | 4 | 3.5 | 3.5 | 3.5 | 4 | 3 | 3.58333 | 3.5 | 2 | |
| 6 a | 3.5 | 3.5 | 4 | 3.5 | 4 | 3.5 | 3.66667 | 3.5 | 3 | |
| 7 a | 3.5 | 3 | 3 | 3 | 3 | 3 | 3.08333 | 3 | 2 | |
| 8 a | 4 | 3 | 3.5 | 3 | 3.5 | 3 | 3.33333 | 3 | 2 | |
| 1 b | 5 | 5 | 5 | 4 | 5 | 3.5 | 4.58333 | 5 | 5 | |
| 2 b | 5 | 5 | 5 | 5 | 5 | 4 | 4.83333 | 5 | 3.5 | |
| 3 b | 5 | 5 | 4 | 4 | 4 | 3.5 | 4.25 | 4 | 4 | |
| 4 b | 5 | 4 | 4 | 4 | 4 | 3.5 | 4.08333 | 4 | 5 | |
| 5 b | 5 | 5 | 5 | 5 | 5 | 4 | 4.83333 | 5 | 3.5 | |
| 6 b | 5 | 5 | 5 | 5 | 5 | 3.5 | 4.75 | 5 | 3 | |
| 7 b | 4 | 5 | 4 | 4 | 3.5 | 3.5 | 4 | 4 | 4 | |
| 8 b | 5 | 4 | 4 | 4 | 4 | 3 | 4 | 4 | 3.5 | |
| 1 c | 4 | 3 | 3.5 | 3.5 | 3.5 | 3 | 3.41667 | 3.5 | 2 | |
| 2 c | 3.5 | 3 | 4 | 4 | 3.5 | 3.5 | 3.58333 | 3.5 | 2 | |
| 3 c | 3 | 3 | 3 | 3 | 3 | 3 | 3 | 3 | 2 | |
| 4 c | 2 | 2 | 3 | 2 | 2 | 2 | 2.16667 | 2 | 1 | |
| 5 c | 4 | 4 | 4 | 4 | 4 | 3.5 | 3.91667 | 4 | 1 | |
| 6 c | 3 | 3.5 | 3 | 3 | 3 | 2 | 2.91667 | 3 | 1 | |
| 7 c | 3 | 3 | 3 | 3 | 3 | 3 | 3 | 3 | 2 | |
| 8 c | 4 | 3.5 | 3 | 3 | 3.5 | 3 | 3.33333 | 3 | 2 | |

From Table 8, the grades from the plane-cutting algorithm are neither consistent with the grades by technicians, and the correlation coefficient between them is about 74.5%. There are two reasons accounting for this. On one hand, the replicas are made of plastic materials, whose surfaces are different from those of fabric specimens. They are smooth and not hairy while the fabric specimens have hairiness on surfaces. On the other hand, the wrinkle sizes of the specimens and the replicas are different. For example, it is observed that the No. 1 wrinkles of fabrics are always larger than the No. 1 wrinkles of replicas. In addition, the blurring window sizes are chosen to be small. There are some damages on wrinkles of both replicas and specimens while highlighting crease-shaped wrinkles. The results are observed to be very sensitive to the blurring window sizes. Using the window sizes WS1=15 and WS2=5, the grades of all fabric specimens are shown in Table 9. The correlation coefficient between the grades from the algorithm and by technicians is about 82.6%. However, the inconsistence still exists between the algorithm-grades and the technician-grades.

So far the application results of two algorithms have been presented above. Each algorithm gets a certain degree of success to classify the six replicas but does not perform well to classify all the fabric specimens. The wrinkle grades from both algorithms are not completely consistent with those grades by technicians.

TABLE 9

| Sample ID | Tech1 First | Tech1 Second | Tech2 First | Tech2 Second | Tech3 First | Tech3 Second | Average all | Final grades | P-Cutting grades | Correl. Coeff. |
|---|---|---|---|---|---|---|---|---|---|---|
| 1TT | 3 | 3 | 2 | 3 | 3 | 3 | 2.83333 | 3 | 2 | 82.63% |
| 2TT | 2 | 2 | 2 | 2 | 2 | 2 | 2 | 2 | 2 | |
| 3TT | 3 | 3 | 3 | 3 | 3 | 3.5 | 3.08333 | 3 | 3 | |
| 4TT | 3 | 3 | 3 | 3 | 3 | 2 | 2.83333 | 3 | 3 | |
| 5TT | 1 | 1 | 1 | 2 | 2 | 2 | 1.5 | 1 | 1 | |
| 6TT b | 5 | 5 | 5 | 5 | 5 | 4 | 4.83333 | 5 | 5 | |
| 7TT | 3 | 3 | 3 | 3 | 3 | 3 | 3 | 3 | 3 | |
| 8TT | 2 | 2 | 2 | 1 | 2 | 2 | 1.83333 | 2 | 2 | |
| 9TT a | 4 | 4 | 3 | 3.5 | 3.5 | 3.5 | 3.58333 | 3.5 | 3.5 | |
| 10TT | 1 | 1 | 2 | 1 | 3 | 1 | 1.5 | 1 | 1 | |
| 11TT b | 5 | 5 | 5 | 5 | 5 | 3.5 | 4.75 | 5 | 5 | |
| 12TT | 1 | 1 | 1 | 1 | 2 | 1 | 1.16667 | 1 | 1 | |
| 13TT a | 4 | 4 | 3 | 3.5 | 3 | 3 | 3.41667 | 3.5 | 4 | |
| 14TT b | 5 | 5 | 5 | 5 | 5 | 4 | 4.83333 | 5 | 5 | |
| 15TT | 3 | 3 | 3 | 3 | 3 | 3 | 3 | 3 | 3 | |
| 16TT | 2 | 3 | 2 | 2 | 2 | 3 | 2.33333 | 2 | 2 | |
| 17TT | 3 | 3.5 | 3 | 3 | 3 | 3 | 3.08333 | 3 | 2 | |
| 18TT a | 4 | 4 | 3.5 | 3.5 | 3 | 3 | 3.5 | 3.5 | 4 | |
| 1 a | 3.5 | 4 | 3.5 | 4 | 3 | 3.5 | 3.58333 | 3.5 | 4 | |
| 2 a | 3.5 | 3 | 3.5 | 4 | 3 | 3.5 | 3.41667 | 3.5 | 2 | |
| 4 a | 4 | 3.5 | 3.5 | 3.5 | 3.5 | 3.5 | 3.58333 | 3.5 | 3 | |
| 5 a | 4 | 3.5 | 3.5 | 3.5 | 4 | 3 | 3.58333 | 3.5 | 3 | |
| 6 a | 3.5 | 3.5 | 4 | 3.5 | 4 | 3.5 | 3.66667 | 3.5 | 3.5 | |
| 7 a | 3.5 | 3 | 3 | 3 | 3 | 3 | 3.08333 | 3 | 2 | |

TABLE 9-continued

| Sample ID | Tech1 First | Tech1 Second | Tech2 First | Tech2 Second | Tech3 First | Tech3 Second | Average all | Final grades | P-Cutting grades | Correl. Coeff. |
|---|---|---|---|---|---|---|---|---|---|---|
| 8 a | 4 | 3 | 3.5 | 3 | 3.5 | 3 | 3.33333 | 3 | 2 | |
| 1 b | 5 | 5 | 5 | 4 | 5 | 3.5 | 4.58333 | 5 | 4 | |
| 2 b | 5 | 5 | 5 | 5 | 5 | 4 | 4.83333 | 5 | 4 | |
| 3 b | 5 | 5 | 4 | 4 | 4 | 3.5 | 4.25 | 4 | 3.5 | |
| 4 b | 5 | 4 | 4 | 4 | 4 | 3.5 | 4.08333 | 4 | 4 | |
| 5 b | 5 | 5 | 5 | 5 | 5 | 4 | 4.83333 | 5 | 4 | |
| 6 b | 5 | 5 | 5 | 5 | 5 | 3.5 | 4.75 | 5 | 3.5 | |
| 7 b | 4 | 5 | 4 | 4 | 3.5 | 3.5 | 4 | 4 | 4 | |
| 8 b | 5 | 4 | 4 | 4 | 4 | 3 | 4 | 4 | 4 | |
| 1 c | 4 | 3 | 3.5 | 3.5 | 3.5 | 3 | 3.41667 | 3.5 | 3 | |
| 2 c | 3.5 | 3 | 4 | 4 | 3.5 | 3.5 | 3.58333 | 3.5 | 2 | |
| 3 c | 3 | 3 | 3 | 3 | 3 | 3 | 3 | 3 | 2 | |
| 4 c | 2 | 2 | 3 | 2 | 2 | 2 | 2.16667 | 2 | 1 | |
| 5 c | 4 | 4 | 4 | 4 | 4 | 3.5 | 3.91667 | 4 | 2 | |
| 6 c | 3 | 3.5 | 3 | 3 | 3 | 2 | 2.91667 | 3 | 1 | |
| 7 c | 3 | 3 | 3 | 3 | 3 | 3 | 3 | 3 | 2 | |
| 8 c | 4 | 3.5 | 3 | 3 | 3.5 | 3 | 3.33333 | 3 | 2 | |

Discussion

Figure 23:
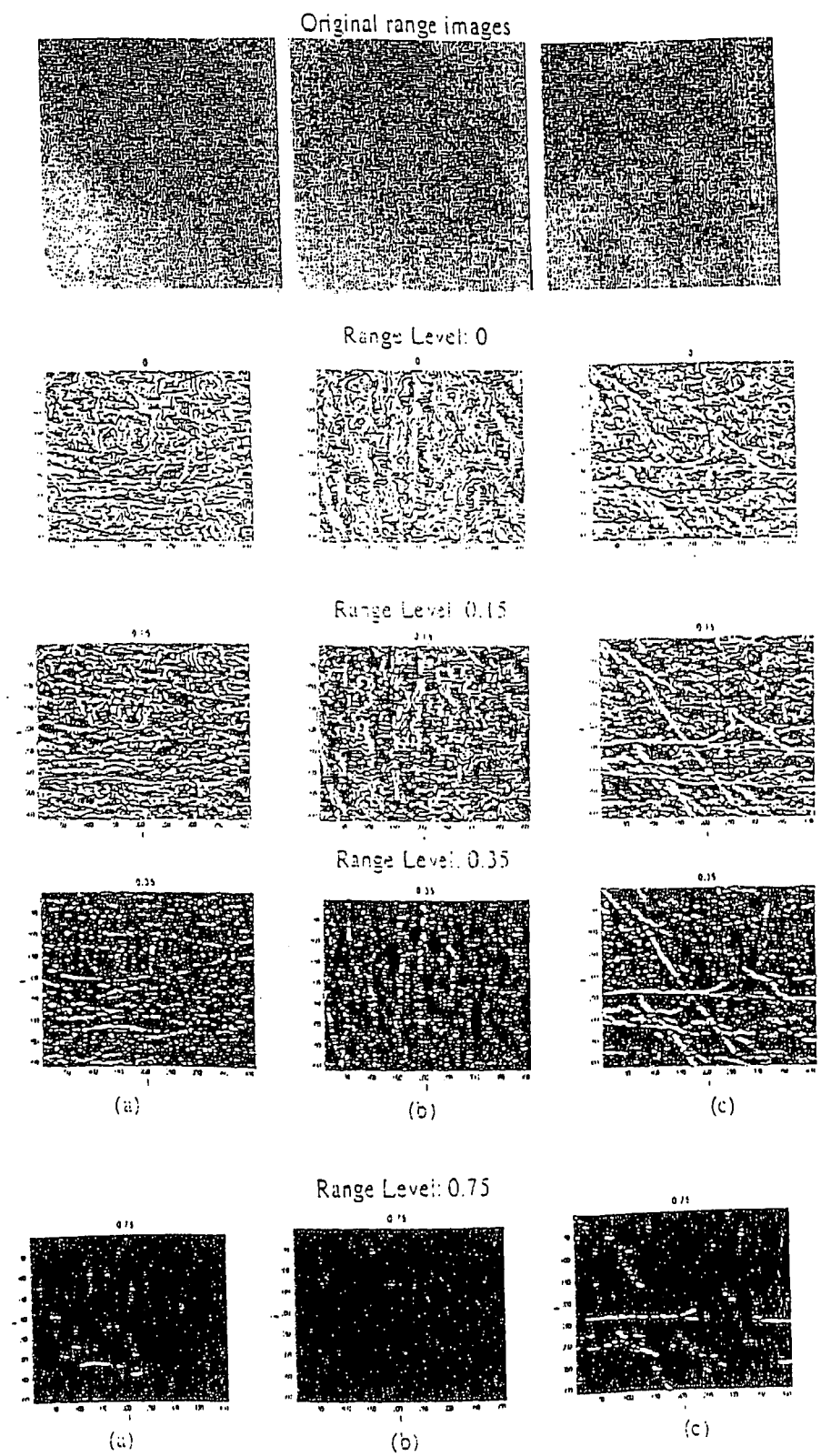
FIG. 23 shows binary images of intersected areas at the relevant range levels (a) CTR No. 3 replicas, (b) CTR No. 3.5 replicas, and (c) fabric sample 7a (WS1=9, WS2=5)

The small blurring window sizes are particularly chosen to enhance and extract the special wrinkles-creases. To indicate the effect from the small blurring window sizes, FIG. 23 shows some binary images of the intersected areas at the relevant range levels in the plane-cutting algorithm. The samples used here are (a) the central part of the No. 3 replica, (b) the central part of the No. 3.5 replica, and (c) the fabric sample 7a. (Note: In each binary image the white pixels are 1, otherwise the pixels are 0).

Figure 24:
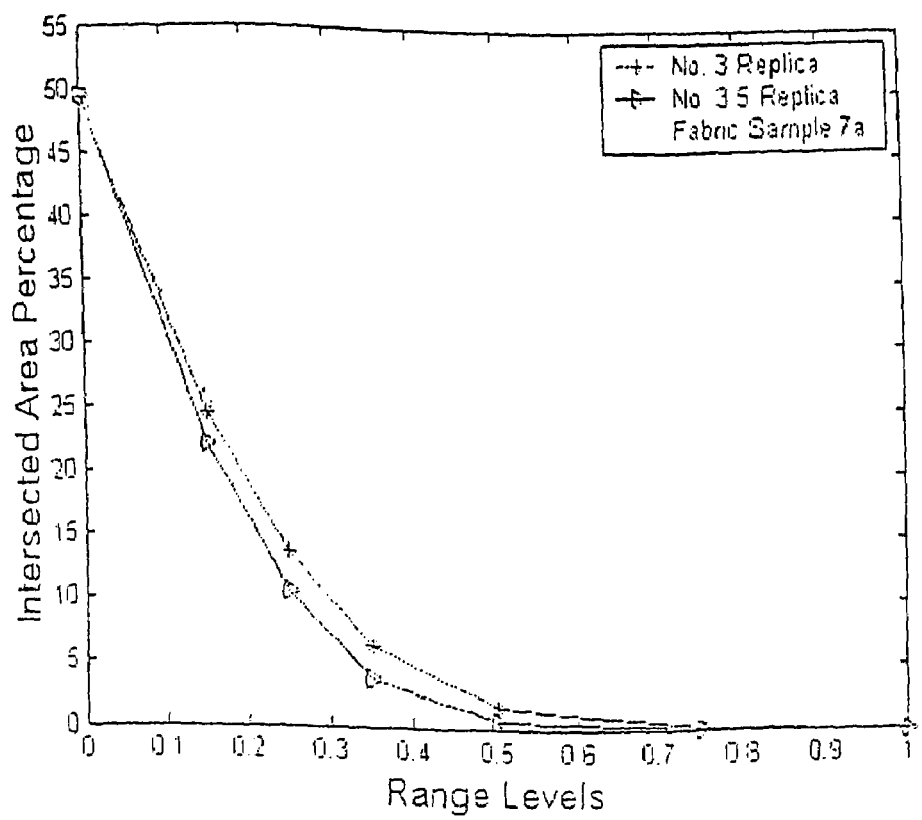
FIG. 24 shows a plot of intersected area percentage versus range levels.

The range images of the three samples are shown in the first row of FIG. 4.8. If the range level of a cutting plane is set to zero during the plane-cutting algorithm, the three samples are almost the same results with ones occupying about 50% of the whole image (the images shown in the second row of FIG. 23) With the range levels greater than zero, the percentages of intersected areas over the whole images are getting different. Through calculating the values log(Ω) in the plane-cutting algorithm, highlighted are the creases in Replica No. 3, different from the general wrinkles in Replica No. 3.5. Especially when the range level is 0.35, these creases of the sample 7a are obviously extracted out. The differences are also shown through the curves of intersected area percentage versus range levels during the plane-cutting algorithm (FIG. 24.

After pixel subtraction with larger blurring window sizes such as WS1=91 and WS2=11 used in the facet model algorithm, these creases are almost removed due to the averaging function in blurring.

One of the main interference factors in the two algorithms is the hairy surfaces of the fabric specimens. This interference factor is embedded while the laser camera system is used, so first take a close look at the profiling algorithm of the laser camera and check how hairy surfaces affect range images.

Figure 25:
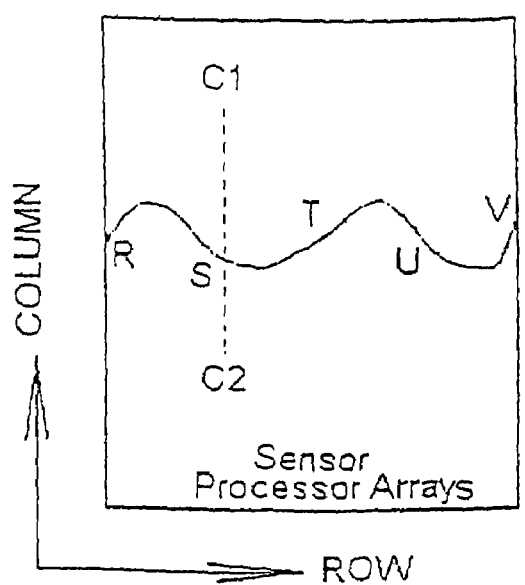
FIG. 25 shows a horizontal sheet-of-light range imaging of the sensor.

FIG. 25 shows the sketch of the sensor processor arrays of the laser-camera. The curve of RSTUV shown in the figure is a profile from the laser line. The range laser camera first uses a threshold to find the laser shining over all the region of the processor arrays. Then it finds one maximum-intensity pixel among the pixels of each column (for example, C1C2 and locates the maximum pixel as the final pixel of that column. Each column has one pixel and the pixels of all columns make up a profile.

Take a close look at the laser line on a hairy surface. Because the laser projector is tilted at an angle 80°, some shaggy hairiness catches the laser line and reflects a bright point, whose intensity might be the maximum along the column directions. Therefore the range image looks ugly and noisy due to the hairy surfaces.

Although in each algorithm there are smoothening steps such as a notch filter and blurring the influence of hairy surfaces is still brought into calculating the values of Θ and log(Ω). These values of fabric specimens with hairy surfaces are generally larger than those of other specimens of the same technician-grades. The fabric specimens have more or less, such hairy surfaces. That is also one of the reasons why most values of Θ and log(Ω) of the fabrics are larger than those of the replicas.

Figure 26:
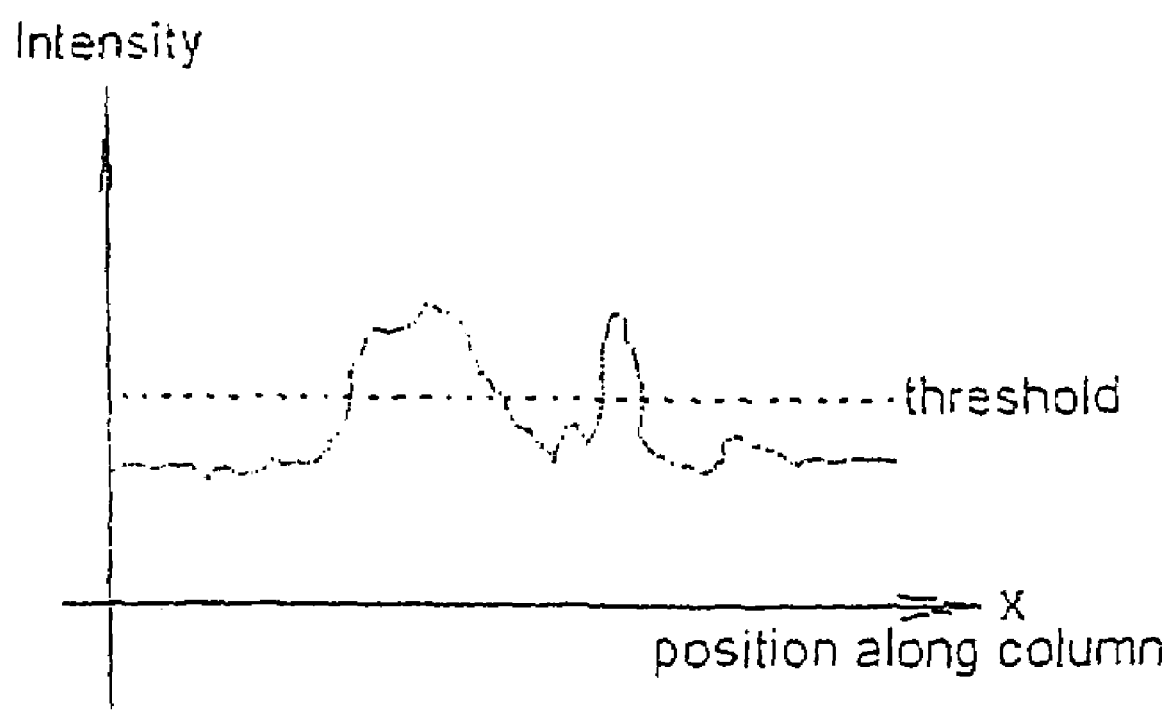
FIG. 26 is an illustration of finding the laser reflection.

This problem of hairy surfaces might be resolved if the laser camera sensor could use a center-of-gravity technique. Suppose the intensity distribution along C1C2 is the line shown in FIG. 26. After applying a threshold, the center-of-gravity position using the total signal along the column is set as the position in that column, given by the equation $$\text{position} = \frac{\sum_x x I(x)}{\sum_x I(x)}, \quad \text{(Eq. 4.1)}$$

where x is the pixel column position and I(x) is the pixel intensity. With the help of the center-of-gravity technique, the range images of these hairy-surfaced fabrics might be smoother. However, with this method, the resolution along the column direction of range images might be decreased. Especially when fabric specimens or replicas have some creases, the resolution for detecting those creases may be affected.

CONCLUSIONS

The following conclusions are drawn from the discussion and results in the previous section:
1. The laser-camera system is set up particularly for capturing range images of wrinkles on replicas and fabric specimens. It works well for general fabric specimens, but if fabric specimens are very hairy, the range images obtained are noisy and cannot indicate small wrinkles and creases.

2. A facet model algorithm is introduced in detail and applied in evaluating wrinkles. Experiments show that the topographic labels from the algorithm reveal the information of wrinkles.
3. Developed from the facet model algorithm, a plane-cutting algorithm is presented and it is simple and easy to apply. Both of the algorithms work well to classify replicas.
4. The inconsistence between the grades from both algorithms and the grades by technicians implies that further research is required.

Examples

For real continuous functions f(x) and g(x) with x∈[a b], the inner product is defined as:

$$\langle f(x), g(x) \rangle = \int_a^b f(x)g(x)\,dx. \tag{A.1}$$

Consider the set of continuous functions C[a, b], and the powers of x, $\{1, x, x^2, \ldots, x^n\}$, which on any interval [a b] (a≠b) form a linearly independent set. Take [a, b]=[−1, 1], and the inner product is written as:

$$\langle f(x), g(x) \rangle = \int_{-1}^1 f(x)g(x)\,dx. \tag{A.2}$$

Using the Gram-Schmidt procedure shown in Eq. 3.4, we find $$P_1 = 1,\ P_2 = x,\ P_3 = x^2 - 1/3,\ P_4 = x^3 - 3x/5, \tag{A.3}$$

and so on. The functions thus generated as $P_i(i=1,2\ldots n)$ are called the Legendre Polynomials and they are mutually orthogonal on the interval [−1, 1].

In a 2D coordinate, there are two discrete functions f(r,c) and (r(r,c). Here, (r,c) belong to the region of facet model window Ψ. That is, r and c are integers. Consider a n×n facet model window (n is odd), then r∈[−(n−1)/2, (n−1)/2)] and c∈[−(n−1)/2, (n−1)/2)]. Then the inner product of these two discrete functions is defined as:

$$\langle f(r,c), g(r,c) \rangle = \frac{1}{n^2} \sum_{r=-\frac{n-1}{2}}^{\frac{n-1}{2}} \sum_{c=-\frac{n-1}{2}}^{\frac{n-1}{2}} f(r,c)g(r,c). \tag{A.4}$$

Taken as an example, one 5×5 facet model window is defined, then r∈[−2, 2] and c∈[−2,2] as shown in FIG. 3.9 where there is a 7×7 facet model window. The inner product of these two discrete functions f(r,c) and g(r,c) is defined as:

$$\langle f(r,c), g(r,c) \rangle = \frac{1}{25} \sum_{r=-2}^{2} \sum_{c=2}^{2} f(r,c)g(r,c). \tag{A.5}$$

For example, if f(r,c)=1, and g(r,c)=r, then, $$\langle f(r,c), g(r,c) \rangle_{5 \times 5} = \langle 1, r \rangle_{5 \times 5} = \frac{1}{25} \sum_{r=-2}^{2} \sum_{c=-2}^{2} r = 0. \tag{A.6}$$

Considering the linearly independent set $\{x_1, x_2, x_3, \ldots x_{10}\} = \{1, r, c, r^2, rc, c^2, r^3 r^3 c, rc^2, c^3\}$ on the region of the 5×5 facet model window and set $P_1 = x_1 = 1$, we can obtain an orthogonal set using Eq. 3.4.

$$P_2 = r - \frac{<r, P_1> P_1}{<P_1, P_1>} = r - \frac{<r, 1>}{<1, 1>} = r - 0 = r,$$

$$P_3 = c - \frac{<c, 1>}{<1, 1>} - \frac{<c, r> r}{<r, r>} = c - 0 - 0 = c,$$

$$P_4 = r^2 - \frac{<r^2, 1>}{<1, 1>} - \frac{<r^2, r> r}{<r, r>} - \frac{<r^2, c> c}{<c, c>} = r^2 - 2 - 0 - 0 = r^2 - 2,$$

$$P_5 = rc - \frac{<rc, 1>}{<1, 1>} - \frac{<rc, r> r}{<r, r>} - \frac{<rc, c> c}{<c, c>} - \frac{<rc, r^2-2>(r^2-2)}{<r^2-2, r^2-2>} = rc - 0 - 0 - 0 = rc,$$

$$P_6 = c^2 - \frac{<c^2, 1>}{<1, 1>} - \frac{<c^2, r> r}{<r, r>} - \frac{<c^2, c> c}{<c, c>} - \frac{<c^2, r^2-2>(r^2-2)}{<r^2-2, r^2-2>} - \frac{<c^2, rc> rc}{<rc, rc>}$$
$$= c^2 - 2 - 0 - 0 - 0 = c^2 - 2$$

$$P_7 = r^3 - \frac{<r^3, 1>}{<1, 1>} - \frac{<r^3, r> r}{<r, r>} - \frac{<r^3, c> c}{<c, c>} - \frac{<r^3, r^2-2>(r^2-2)}{<r^2-2, r^2-2>} - \frac{<r^3, rc> rc}{<rc, rc>} - \frac{<r^3, c^2-2>(c^2-2)}{<c^2-2, c^2-2>}$$
$$= r^3 - 0 - \frac{34 \times 5/25}{10 \times 5/25} - 0 - 0 - 0 = r^3 - 3.4r$$

The following results are also obtained as shown in Eq. 3.5:

$$P_8(r,c) = r^2 c - 2c,$$

$$P_9(r,c) = rc^2 - 2r,$$

$$P_{10}(r,c) = c^3 - 3.4c.$$

Considering a 5×5 facet model window and use the set of linear polynomials $\{x_1, x_2, x_3, \ldots x_{10}\} = \{1, r, c, r^2, rc, c^2, r^3, r^2 c, rc^2, c^3\}$, we can obtain a mutually orthogonal set as shown in both Appendix B and Eq. 3.5. It is:

$$P_1(r,c) = 1 \quad P_2(r,c) = r \quad P_3(r,c) = c \tag{B.1}$$
$$P_4(r,c) = r^2 - 2 \quad P_5(r,c) = rc \quad P_6(r,c) = c^2 - 2$$
$$P_7(r,c) = r^3 - 3.4r \quad P_8(r,c) = \quad P_9(r,c) = rc^2 - 2r$$
$$\quad\quad r^2 c - 2c$$
$$P_{10}(r,c) = c^3 - 3, 4c$$

According to Eq. 3.11, $$a_m = \frac{\sum_{(r,c)\in\Psi} P_m(r,c)d(r,c)}{\sum_{(r,c)\in\Psi} P_m^2(r,c)}, m=1,2,\ldots,10,$$

the convenience of using an orthogonal basis set is utilized during the procedure of solving $a_m$ since the values of $$\sum_{(r,c)\in\Psi} P_m(r,c) \sum_{(r,c)\in\Psi} P_{m'}(r,c),$$

(here $m \neq m'$, $m=1, 2, \ldots, 10$, $m'=1, 2, \ldots, 10$) are zero. Eq. (3.11) is interesting because it means that each fitting coefficient $a_m$ can be computed as a linear combination of the gray level data of $d(r,c)$. For each pixel over the related window $\Psi$, the gray level value $d(r,c)$ is multiplied by the weight $$W_m(r,c) = \frac{P_m(r,c)}{\sum_{(r,c)\in\Psi} P_m^2(r,c)}. \quad (B.2)$$

Now using B.2 (i.e. Eq. 3.12), we could obtain filters over a 5×5 window.

$m=1$, $P_1(r,c)=1$

| $W_1 = 1/25X$ | 1 | 1 | 1 | 1 | 1 |
|---|---|---|---|---|---|
| | 1 | 1 | 1 | 1 | 1 |
| | 1 | 1 | 1 | 1 | 1 |
| | 1 | 1 | 1 | 1 | 1 |
| | 1 | 1 | 1 | 1 | 1 |

$m=2$, $P_2(r,c)=r$

| $W_2 = 1/50X$ | -2 | -2 | -2 | -2 | -2 |
|---|---|---|---|---|---|
| | -1 | -1 | -1 | -1 | -1 |
| | 0 | 0 | 0 | 0 | 0 |
| | 1 | 1 | 1 | 1 | 1 |
| | 2 | 2 | 2 | 2 | 2 |

$m=3$, $P_3(r,c)=c$

| $W_3 = 1/50X$ | -2 | -1 | 0 | 1 | 2 |
|---|---|---|---|---|---|
| | -2 | -1 | 0 | 1 | 2 |
| | -2 | -1 | 0 | 1 | 2 |
| | -2 | -1 | 0 | 1 | 2 |
| | -2 | -1 | 0 | 1 | 2 |

$m=4$, $P_4(r,c)=r^2-2$

| $W_4 = 1/70X$ | 2 | 2 | 2 | 2 | 2 |
|---|---|---|---|---|---|
| | -1 | -1 | -1 | -1 | -1 |
| | -2 | -2 | -2 | -2 | -2 |
| | -1 | -1 | -1 | -1 | -1 |
| | 2 | 2 | 2 | 2 | 2 |

$m=5$, $P_5(r,c)=rc$

| $W_5 = 1/100X$ | 4 | 2 | 0 | -2 | -4 |
|---|---|---|---|---|---|
| | 2 | 1 | 0 | -1 | -2 |
| | 0 | 0 | 0 | 0 | 0 |
| | -2 | -1 | 0 | 1 | 2 |
| | -4 | -2 | 0 | 2 | 4 |

$m=6$, $P_6(r,c)=c^2-2$

| $W_6 = 1/70X$ | 2 | -1 | -2 | -1 | 2 |
|---|---|---|---|---|---|
| | 2 | -1 | -2 | -1 | 2 |
| | 2 | -1 | -2 | -1 | 2 |
| | 2 | -1 | -2 | -1 | 2 |
| | 2 | -1 | -2 | -1 | 2 |

$m=7$, $P_7(r,c)=r^3-3.4r$

| $W_7 = 1/50X$ | -1 | -1 | -1 | -1 | -1 |
|---|---|---|---|---|---|
| | 2 | 2 | 2 | 2 | 2 |
| | 0 | 0 | 0 | 0 | 0 |
| | -2 | -2 | -2 | -2 | -2 |
| | 1 | 1 | 1 | 1 | 1 |

$m=8$, $P_8(r,c)=r^2c-2c$

| $W_8 = 1/140X$ | -4 | -2 | 0 | 2 | 4 |
|---|---|---|---|---|---|
| | 2 | 1 | 0 | -1 | -2 |
| | 4 | 2 | 0 | -2 | -4 |
| | 2 | 1 | 0 | -1 | -2 |
| | -4 | -2 | 0 | 2 | 4 |

$m=9$, $P_9(r,c)=rc^2-2r$

| $W_9 = 1/140X$ | -4 | 2 | 4 | 2 | -4 |
|---|---|---|---|---|---|
| | -2 | 1 | 2 | 1 | -2 |
| | 0 | 0 | 0 | 0 | 0 |
| | 2 | -1 | -2 | -1 | 2 |
| | 4 | -2 | -4 | -2 | 4 |

$m=10$, $P_{10}(r,c)=c^3-3.4c$

| $W_{10} = 1/50X$ | -1 | 2 | 0 | -2 | 1 |
|---|---|---|---|---|---|
| | -1 | 2 | 0 | -2 | 1 |
| | -1 | 2 | 0 | -2 | 1 |
| | -1 | 2 | 0 | -2 | 1 |
| | -1 | 2 | 0 | -2 | 1 |

So far we could calculate the coefficients $a_m$ in Eq. 3.11. For example, suppose we have a neighborhood area at the pixel (i,j) shown in the following figure. D(r,c) is the matrix of the gray values in this neighborhood.

FIG. B.1. The gray value of the neighborhood at the pixel (i, j)

$$D(r, c) = \begin{pmatrix} 20 & 30 & 20 & 40 & 10 \\ 20 & 10 & 10 & 50 & 100 \\ 10 & 30 & 40 & 30 & 20 \\ 30 & 50 & 50 & 20 & 20 \\ 80 & 70 & 60 & 50 & 10 \end{pmatrix}$$

The pixel (i, j)

Then the coefficients could be obtained as follows (calculating pixel correlation):

$a_1 = W_1 \otimes D(r,c)$

That is, $$a_1 = 1/25 \times \begin{pmatrix} 1 & 1 & 1 & 1 & 1 \\ 1 & 1 & 1 & 1 & 1 \\ 1 & 1 & 1 & 1 & 1 \\ 1 & 1 & 1 & 1 & 1 \\ 1 & 1 & 1 & 1 & 1 \end{pmatrix} \otimes \begin{pmatrix} 20 & 30 & 20 & 40 & 10 \\ 20 & 10 & 10 & 50 & 100 \\ 10 & 30 & 40 & 30 & 20 \\ 30 & 50 & 50 & 20 & 20 \\ 80 & 70 & 60 & 50 & 10 \end{pmatrix}$$

$a_1 =$ $$\begin{pmatrix} 0.0400 & 0.0400 & 0.0400 & 0.0400 & 0.0400 \\ 0.0400 & 0.0400 & 0.0400 & 0.0400 & 0.0400 \\ 0.0400 & 0.0400 & 0.0400 & 0.0400 & 0.0400 \\ 0.0400 & 0.0400 & 0.0400 & 0.0400 & 0.0400 \\ 0.0400 & 0.0400 & 0.0400 & 0.0400 & 0.0400 \end{pmatrix} \otimes \begin{pmatrix} 20 & 30 & 20 & 40 & 10 \\ 20 & 10 & 10 & 50 & 100 \\ 10 & 30 & 40 & 30 & 20 \\ 30 & 50 & 50 & 20 & 20 \\ 80 & 70 & 60 & 50 & 10 \end{pmatrix}$$

i.e., $a_1 = 35.2$.

With the same method, the following coefficients are obtained:

$a_2 = 5.6$,
$a_3 = 0$,
$a_4 = 2.2857$,
$a_5 = 5.5$,
$a_6 = 1.4286$,
$a_7 = 3.8$,
$a_8 = 3.7857$,
$a_9 = 1.7857$,
$a_{10} = 15.2$.

Using Eq. 3.13, the coefficients of $k_i (i=1,2, \ldots, 10)$ in Eq. 3.1 could be calculated.

Although the present invention has been disclosed in terms of a preferred embodiment, it will be understood that numerous additional modifications and variations could be made thereto without departing from the scope of the invention as defined by the following claims:

What is claimed is:

1. An active imaging system for determining the smoothness of the surface of a fabric, the system comprising:
   a support for holding the fabric in a plane;
   a single-line laser projector positioned at an angle above said plane, the single-line laser projector capable of directing radiation onto at least one portion of the surface of the fabric;
   a single range camera positioned above said plane, the range camera capable of capturing at least one range image of the at least one portion of the surface of the fabric based on the radiation from only the single-line laser projector, the range image including a topographic map including height differences of a plurality of points on the surface of the at least one portion of the surface of the fabric; and
   a processor that obtains the range image, and determines the smoothness of the surface of the fabric using an algorithm that incorporates one of a facet model and a plane-cutting method,
   wherein,
   the smoothness of the surface is determined by:
      generating a plurality of parallel planes that intersect the surface at a plurality of range levels,
      recording an intersection area with the surface for each of the parallel planes,
      calculating a category of a plurality of categories for each of the intersection areas, the plurality of categories including an area under the curve of the intersection area versus the range level, and
      determining a degree of smoothness for the surface.

2. The system of claim 1, wherein the range camera is a CMOS camera.

3. The system of claim 1, wherein the support is a platform with a planar surface for supporting the fabric.

4. The system of claim 3, wherein the planar surface is parallel to the optics plane of the range camera.

5. The system of claim 3, wherein the planar surface is perpendicular to a line of sight of the range camera.

6. The system of claim 1, wherein the range camera is at least 21 inches above the support.

7. The system of claim 1, wherein the single-line laser projector is capable of directing radiation at the support along a line of sight approximately 80 degrees away from a line of sight of the range camera.

8. The system of claim 1, wherein the single-line laser projector, the sensor and the support are arranged substantially in a triangle.

9. The system of claim 1, wherein the range camera moves over the support to capture the range image of the surface of the fabric.

10. The system of claim 1, wherein the support moves along a plane parallel to an optics plane of the range camera.

11. The system of claim 1, wherein the range camera captures the at least one range image based on radiation, from the projector, that is reflected from the surface of the fabric.

12. The system of claim 11, wherein the topographic data comprises at least one height of a point in the surface of the fabric relative to the at least one reference point.

13. The system of claim 1, wherein the processor preprocesses the range image by enhancing wrinkles on the surface of the fabric.

14. The system of claim 1, wherein the smoothness of the surface is determined by
   approximating the surface using a facet model to provide a piece-wise continuous surface of connected facets;
   calculating a category of a plurality of categories for each of the connected facets, the plurality of categories including at least one of slope, ridge, peak, ravine, and pit; and
   determining a degree of smoothness for connected facets that are proximate to each other.

15. The system of claim 1, wherein the processor extracts features on the surface to quantify the smoothness.

16. A method for detecting wrinkles in a surface of a fabric using a topographic map of the surface to determine a smoothness of the surface of the fabric, the method comprising:

positioning a single-line laser projector at an angle over a plane supporting the fabric;

directing radiation onto at least one portion of the surface of the fabric from only the single-line laser projector;

obtaining a range image of the at least one portion of the surface of the fabric based on the directed radiation by using a single range camera, the range image including a topographic map including height differences of a plurality of points on the surface of the at least one portion of the surface of the fabric; and determining the smoothness of the surface of the fabric using an algorithm that incorporates one of a facet model and a plane-cutting method, wherein, the smoothness of the surface is determined by:

generating a plurality of parallel planes that intersect the surface at a plurality of range levels, recording an intersection area with the surface for each of the parallel planes, calculating a category of a plurality of categories for each of the intersection areas, the plurality of categories including an area under the curve of the intersection area versus the range level, and determining a degree of smoothness for the surface.

17. The method of claim 16, wherein the processor preprocesses the range image by enhancing wrinkles on the surface of the fabric.

18. The method of claim 16, wherein the smoothness of the surface is determined by approximating the surface using a facet model to provide a piece-wise continuous surface of connected facets;

calculating a category of a plurality of categories for each of the connected facets, the plurality of categories including at least one of slope, ridge, peak, ravine, and pit; and determining a degree of smoothness for connected facets that are proximate to each other.

19. The method of claim 16, wherein the processor extracts features on the surface to quantify the smoothness.

20. A method for detecting wrinkles in a surface of a fabric using a topographic map of the surface to determine a smoothness of the surface of the fabric, the method comprising:

obtaining a range image of at least one portion of the surface of the fabric, the range image including a topographic map including height differences of a plurality of points on the surface of the at least one portion of the surface of the fabric; and determining the smoothness of the surface of the fabric using an algorithm that incorporates one of a facet model and a plane-cutting method, wherein, the smoothness of the surface is determined by:

generating a plurality of parallel planes that intersect the surface at a plurality of range levels, recording an intersection area with the surface for each of the parallel planes, calculating a category of a plurality of categories for each of the intersection areas, the plurality of categories including an area under the curve of the intersection area versus the range level, and determining a degree of smoothness for the surface.

\* \* \* \* \*